(12) United States Patent
Hanson et al.

(10) Patent No.: US 12,290,550 B1
(45) Date of Patent: *May 6, 2025

(54) COMPOSITIONS AND METHODS FOR TREATING ENDOCRINE DISEASES AND DISORDERS

(71) Applicant: Olfactive Ai, Inc., Mountain View, CA (US)

(72) Inventors: Christopher Hanson, Mountain View, CA (US); William Harries, Colden, NY (US)

(73) Assignee: Olfactive Ai, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/980,129

(22) Filed: Dec. 13, 2024

Related U.S. Application Data

(60) Continuation-in-part of application No. 18/892,760, filed on Sep. 23, 2024, which is a division of application No. 18/615,150, filed on Mar. 25, 2024, now Pat. No. 12,102,664, which is a continuation-in-part of application No. 18/430,796, filed on Feb. 2, 2024, now Pat. No. 12,115,134.

(60) Provisional application No. 63/615,100, filed on Dec. 27, 2023.

(51) Int. Cl.
| | |
|---|---|
| *A61K 38/00* | (2006.01) |
| *A61K 31/085* | (2006.01) |
| *A61K 31/202* | (2006.01) |
| *A61K 38/26* | (2006.01) |

(52) U.S. Cl.
CPC ............ *A61K 38/26* (2013.01); *A61K 31/085* (2013.01); *A61K 31/202* (2013.01)

(58) Field of Classification Search
CPC .... A61K 31/085; A61K 31/202; A61K 38/26; A61K 31/05; A61K 31/11; A61K 31/20; A61K 31/201
See application file for complete search history.

(56) References Cited

U.S. PATENT DOCUMENTS

| | | |
|---|---|---|
| 10,209,239 B1 | 2/2019 | Hanson et al. |
| 12,102,664 B2 * | 10/2024 | Hanson ................ A61K 31/202 |
| 2017/0100353 A1 | 4/2017 | Krasnow et al. |
| 2021/0145768 A1 | 5/2021 | Ley et al. |

FOREIGN PATENT DOCUMENTS

WO   WO-2023131325 A1   7/2023

OTHER PUBLICATIONS

Beito, et al., "Role of Ectopic Olfactory Receptors in the Regulation of the Cardiovascular-Kidney-Metabolic Axis." Life 14.5 (2024): 548.

\* cited by examiner

*Primary Examiner* — Aradhana Sasan
*Assistant Examiner* — Mercy H Sabila
(74) *Attorney, Agent, or Firm* — Francis Law Group

(57) ABSTRACT

Disclosed herein are compounds and ligands, and compositions formed therewith, that modulate insulin secretion and suppress appetite by activating ectopic olfactory receptors. Also disclosed herein are methods for using the compositions to treat endocrine diseases, such as type-2 diabetes, and disorders, such as abnormal insulin secretion.

26 Claims, 2 Drawing Sheets

COMPOSITIONS AND METHODS FOR TREATING ENDOCRINE DISEASES AND DISORDERS

CROSS-REFERENCES TO RELATED APPLICATIONS

This application is a continuation-in-part of U.S. application Ser. No. 18/892,760, filed on Sep. 23, 2024, which is a divisional of U.S. application Ser. No. 18/615,150, filed on Mar. 25, 2024, now U.S. Pat. No. 12,102,664, which is a continuation-in-part of U.S. application Ser. No. 18/430,796, now U.S. Pat. No. 12,115,134, filed on Feb. 2, 2024, which claims the benefit of U.S. Provisional Application No. 63/615,100, filed on Dec. 27, 2023.

FIELD OF THE INVENTION

The present invention relates to compositions and methods for treating endocrine disorders. More particularly, the present invention relates to compositions and methods for treating diabetes mellitus and obesity by modulating ectopic olfactory activity.

BACKGROUND OF THE INVENTION

As is well established, obesity is a disorder that affects the health of millions of adults and youth in the U.S. According to a 2021 Centers for Disease Control and Prevention (CDC) survey, the prevalence of obesity in the U.S. between 2017-2020 was 41.9% in adults (i.e., adults having a body mass index (BMI) of greater than or equal to 30 $kg/m^2$), 9.2% of which being severely obese (i.e., adults having a BMI than or equal to 40 $kg/m^2$), and 19.7% in youth.

Based on earlier CDC data, the above-noted prevalence of adult obesity increased approximately 10% over a ten (10) year period, and the prevalence of youth obesity increased approximately 7% during the same period.

The increasing prevalence of obesity is also a growing U.S. national security concern due to difficulties maintaining operational readiness among current service members and shrinking recruitment pools. An October 2023 study by the American Security Project (ASP) reflects that military obesity rates across active duty personal increased by approximately 11.2% between 2012 and 2022, according to an October 2023 study. The study also reflects that 68% of active duty service members are either overweight or obese, and that eating disorders in the military also increased by approximately 79% between 2017 and 2021.

The rapidly increasing prevalence of obesity is not limited to the U.S. Indeed, the increasing prevalence of obesity is generally regarded as an epidemic worldwide.

In addition to a reduced life expectancy compared to non-obese individuals, and the public stigma and discrimination associated with obesity, obese individuals also often present with diabetes mellitus.

Indeed, the International Diabetes Federation (IDF) reported that in 2021 alone over 300 million obese individuals worldwide were afflicted with diabetes mellitus.

Diabetes mellitus is generally characterized by hyperglycemia associated with abnormal insulin secretion, i.e., insufficient insulin production by the pancreas or insulin resistance exhibited by endogenous cells.

As is well established, in most instances, insulin secretion is induced by pancreatic β-cells when glucagon-like peptide-1 (GLP-1) binds to and activates GLP-1 receptor proteins on endogenous gastrointestinal (GI) cells, such as enteroendocrine L-cells.

In addition to inducing insulin secretion, it has been found that GLP-1 also decreases the rate of gastric emptying and acid secretion, resulting in reduced appetite and, thereby, weight loss.

Obese individuals that present with diabetes mellitus; particularly, type-2 diabetes mellitus, are typically difficult to treat due to long term unhealthy eating patterns and a myriad of physiological complexities associated with the mechanisms of appetite control and energy metabolism. Treatment of such individuals, thus, typically requires significant adjustments in food consumption, and pharmaceutically active agents that increase insulin secretion and/or suppress the appetite of the individual.

Various entities have thus developed pharmaceutically active agents and therapies that treat abnormal insulin secretion. In view of the beneficial metabolic activity induced by GLP-1, the pharmaceutically active agents and associated therapies primarily comprise activation of the GLP-1 receptor proteins on endogenous gastrointestinal (GI) cells.

Such pharmaceutically active agents include semaglutide (Ozempic®, Rybelsus®, Wegovy®), dulaglutide (Trulicity®), exenatide (Bydureon BCise®, Byetta®), and liraglutide (Victoza®, Saxenda®).

The noted pharmaceutically active agents (referred to hereinafter as "GLP-1 analogs") mimic endogenous GLP-1 and are adapted to activate the GLP-1 receptors on endogenous GI cells and, hence, function as GLP-1 receptor agonists.

Although the GLP-1 analogs can effectively activate GLP-1 receptors on pancreatic β-cells and, hence, can induce insulin secretion and suppress the appetite of an individual, there are several drawbacks and disadvantages associated with administration of the GLP-1 analogs to patients.

A major drawback associated with administration of the GLP-1 analogs to patients is the high risk of adverse pathological events. One such adverse pathological event is hypoglycemia (i.e., low blood glucose), which can, and often will, present in patients that are also taking or being administered commonly prescribed antidiabetic agents, such as basal insulin and sulfonylureas.

There is also a high risk of induced production of anti-GLP-1 antibodies and binding of endogenous GLP-1 and the GLP-1 analogs to the anti-GLP-1 antibodies, which can, and often will, induce adverse immune responses.

A further major drawback associated with administration of GLP-1 analogs to individuals are the significant side effects that are often presented by the individuals, including nausea, vomiting, diarrhea, abdominal pain, and constipation.

Since most GLP-1 analogs are administered to patients via a subcutaneous injection, a further drawback associated with GLP-1 analog administration is the pain and discomfort associated with the often-prescribed weekly injections.

Although the GLP-1 analogs developed by Novo Nordisk, which are marketed under the tradename Rybelsus, can also be delivered orally, a significantly greater dose of the Rybelsus GLP-1 analog must be orally administered to an individual to match the pharmacokinetics of the Novo Nordisk injectable GLP-1 analog, which is marketed under the tradename Ozempic, i.e., individuals must be orally administered approximately 100.0 mg/week of the Rybelsus GLP-1 analog to match the efficacy of the typically prescribed 0.5 mg/week of the injectable Ozempic GLP-1 analog.

A further major drawback associated with administration of GLP-1 analogs to individuals is the cost. Indeed, the costs, at present, for a thirty (30) day supply of Ozempic and Rybelsus are approximately $1000.00 and $1200.00, respectively.

As is also well established, in most instances, insulin secretion is also induced by pancreatic β-cells when gastric inhibitory polypeptide (GIP) binds to and activates GIP receptor proteins on the pancreatic β-cells.

Although GIP also induces insulin secretion, there are also several drawbacks and disadvantages associated with administration of GIP alone to patients to treat abnormal insulin secretion.

A major disadvantage is that GIP also induces glucagon secretion from pancreatic β-cells. Since glucagon is a hyperglycemic compound that increases blood sugar when secreted, the increase in glucagon secretion induced by GIP limits its therapeutic potential for treating abnormal insulin secretion.

To address the above noted disadvantage associated with solely activating the GIP receptor proteins on the pancreatic β-cells, Eli Lilly has recently developed a pharmaceutically active agent that activates GLP-1 and GIP receptors on pancreatic β-cells.

The noted pharmaceutically active agent comprises tirzepatide, i.e., a dual GLP-1/GIP analog marketed under the tradenames Mounjaro® and ZepBound®, which provides the beneficial metabolic activity induced by both GLP-1 and GIP in a synergistic manner without a clinically significant increase in glucagon secretion.

Although the dual GLP-1/GIP analogs can effectively activate both GLP-1 and GIP receptors on GI cells and, hence, can induce insulin secretion, many of the drawbacks and disadvantages associated with administration of the GLP-1 analogs alone to patients are also associated with administration of the dual GLP-1/GIP analogs to patients.

Such drawbacks and disadvantages include the significant side effects that are often presented by the individuals, including nausea, vomiting, diarrhea, abdominal pain, kidney problems, and constipation. Indeed, it has been found that approximately 10% of individuals administered dual GLP-1/GIP analogs suffer from the noted side effects.

A further drawback also associated with dual GLP-1/GIP analog administration to patients is the pain and discomfort associated with the often-prescribed weekly injections. Since there are currently no known dual GLP-1/GIP analogs that are approved by the FDA for oral administration, painful weekly subcutaneous injections are the only available route of administration.

A further major drawback that is similarly associated with administration of dual GLP-1/GIP analogs to individuals is the cost. Indeed, the costs, at present, for a thirty (30) day supply of Mounjaro and Zepbound are similarly approximately $1000.00.

There is thus a need for improved compositions and methods to treat type-2 diabetes mellitus, which substantially reduce or overcome the drawbacks and disadvantages associated with the conventional GLP-1 analogs and dual GLP-1/GIP analogs discussed above.

There is also a need for improved compositions and methods to suppress the appetite of obese individuals with minimal side effects.

It is thus one object of the present invention to provide improved compositions and methods for treating type-2 diabetes mellitus that overcome the drawbacks and disadvantages associated with administration of GLP-1 analogs and dual GLP-1/GIP analogs to patients.

It is another object of the present invention to provide improved compositions and methods that can be painlessly administered to patients that present with type-2 diabetes mellitus, which effectively modulate GI cell activity and, thereby, modulate systemic insulin secretion by the GI cells in an individual, without the undesirable side effects associated with administration of GLP-1 analogs and dual GLP-1/GIP analogs to patients.

It is another object of the present invention to provide improved compositions and methods that can be painlessly administered to patients that present with obesity, which effectively suppress the individual's appetite with minimal side effects.

It is another object of the present invention to provide improved compositions that effectively modulate the endocrine system of a patient with minimal side effects, which can be administered to the patient via oral, sublingual, inhalation, intranasal, epidural, intracerebral, transdermal, topical, and injection administration means.

It is another object of the present invention to provide improved compositions that can effectuate olfactory receptor (OR)-mediated secretion of endogenous GLP-1 and PYY in a patient, without the undesirable side effects associated with administration of GLP-1 analogs and dual GLP-1/GIP analogs to patients.

It is another object of the present invention to provide improved compositions that can effectuate OR-mediated secretion of endogenous GIP in a patient, without the undesirable side effects associated with administration of GLP-1 analogs and dual GLP-1/GIP analogs to patients.

It is another object of the present invention to provide improved compositions that can effectuate OR-mediated secretion of endogenous GLP-1 and GIP and in a patient, without the undesirable side effects associated with administration of GLP-1 analogs and dual GLP-1/GIP analogs to patients.

It is another object of the present invention to provide improved compositions that can effectuate free fatty acid receptor-mediated secretion of endogenous GIP in a subject, without the undesirable side effects associated with administration of GLP-1 analogs and dual GLP-1/GIP analogs to patients.

It is another object of the present invention to provide improved compositions that can effectuate transient receptor potential ion channel-mediated secretion of endogenous GIP in a patient, without the undesirable side effects associated with administration of GLP-1 analogs and dual GLP-1/GIP analogs to patients.

It is another object of the present invention to provide improved compositions that can effectuate OR-mediated, free fatty acid receptor-mediated, and transient potential ion channel-mediated secretion of endogenous GLP-1, PYY and GIP in a subject, without the undesirable side effects associated with administration of GLP-1 analogs and dual GLP-1/GIP analogs to patients.

It is another object of the present invention to provide improved compositions that can effectively and safely induce secretion of GLP-1 and/or PYY and/or GIP and, thereby enhanced insulin secretion in vivo, which can be administered to the subject via oral, sublingual, inhalation, intranasal, epidural, intracerebral, transdermal, topical, and injection administration means.

It is another object of the present invention to provide improved compositions that can effectively treat adverse endocrine responses and, hence, endocrine diseases and disorders associated therewith without significant side effects.

SUMMARY OF THE INVENTION

The present invention is directed to compositions and methods for treating endocrine diseases and disorders, and underlying causes thereof.

In some embodiments of the invention, there are thus provided compositions for treating endocrine disorders; particularly, type-2 diabetes mellitus and obesity.

In one embodiment of the invention, the compositions for treating an endocrine disorder (referred to hereinafter as a "GLP-1/GIP secretion composition") comprise (i) a delivery medium, (ii) at least a first receptor activating compound adapted to bind to and activate at least one first receptor selected from the group comprising olfactory receptor family 51 subfamily E member 1 (OR51E1), olfactory receptor family 1 subfamily A member 1 (OR1A1), olfactory receptor family 2 subfamily C member 1 (OR2C1), and olfactory receptor family 10 subfamily J member 5 (OR10J5), and (iii) at least a second receptor activating compound adapted to bind to and activate at least one second receptor selected from the group comprising free fatty acid receptor 1 (FFAR1), free fatty acid receptor 4 (FFAR4), olfactory receptor family 2 subfamily W member 1 (OR2W1), olfactory receptor family 2 subfamily B member 11 (OR2B11), olfactory receptor family 2 subfamily J member 3 (OR2J3), and transient receptor potential cation channel subfamily A member 1 (TRPA1), the GLP-1/GIP secretion composition adapted to effectuate at least glucagon-like peptide-1 (GLP-1) and gastric inhibitory polypeptide (GIP) secretion, and, thereby, increased insulin secretion in vivo.

In a preferred embodiment, the first receptor activating compound comprises a first compound selected from the group comprising 3-methylpentanoic acid, farnesol, eugenol and nonanoic acid.

In a preferred embodiment, the second receptor activating compound comprises a second compound selected from the group comprising a medium-chain free fatty acid, a long-chain free fatty acid and an omega-3 polyunsaturated fatty acid.

In another embodiment of the invention, the compositions for treating an endocrine disorder comprise a GLP-1/GIP secretion composition comprising (i) a delivery medium, (ii) at least a first receptor activating compound adapted to bind to and activate at least one first receptor selected from the group comprising olfactory receptor OR51E1 and olfactory receptor OR2C1, and (iii) at least a second receptor activating compound adapted to bind to and activate at least one second receptor selected from the group comprising free fatty acid receptor FFAR1 and free fatty acid receptor FFAR4, the GLP-1/GIP secretion composition similarly adapted to induce GLP-1 and GIP secretion, and, thereby, increased insulin secretion in vivo, when said GLP-1/GIP secretion composition is delivered to said patient.

In a preferred embodiment, the first receptor activating compound comprises eugenol.

In a preferred embodiment, the second receptor activating compound comprises lauric acid.

In a preferred embodiment, the first receptor activating compounds are adapted to induce at least 50% activation of at least olfactory receptor OR51E1 in vivo.

In a preferred embodiment, the second receptor activating compounds are adapted to induce at least 50% activation of free fatty acid receptor FFAR1 or FFAR4 in vivo.

In some embodiments, the delivery medium comprises ingestible matter, such as an item of food and a beverage.

In a preferred embodiment, when the GLP-1/GIP secretion compositions are delivered to a patient, appetite of the patient is also suppressed.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1:
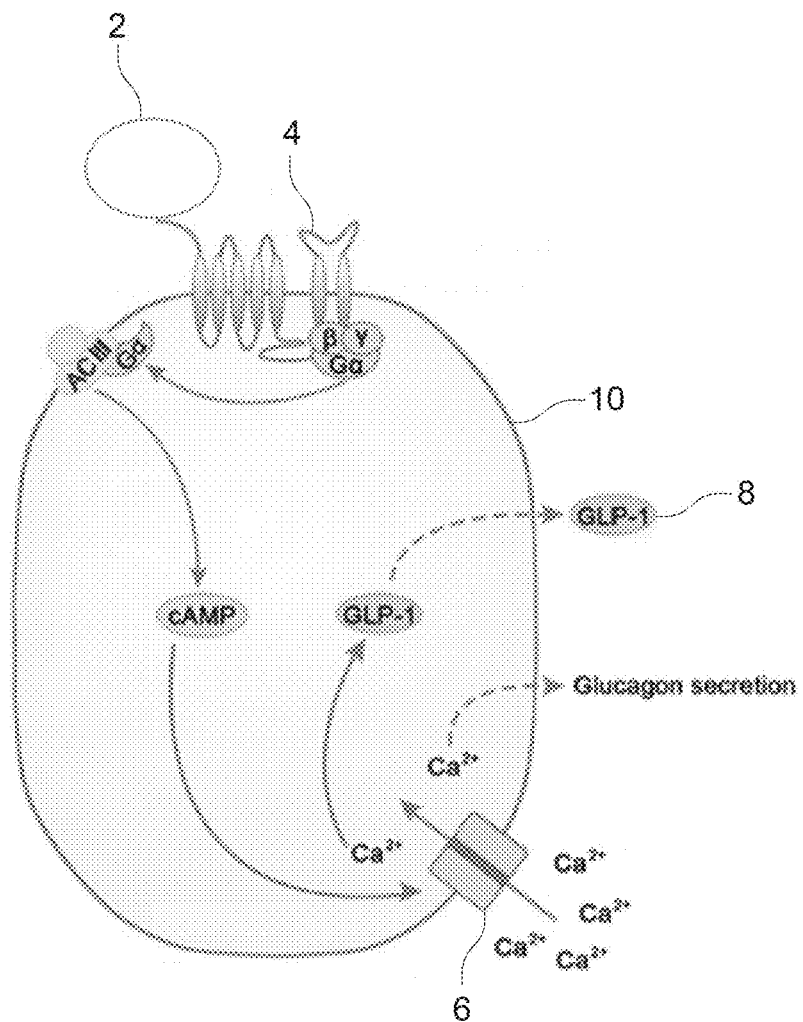
FIG. 1 is a schematic illustration of receptor-mediated activation of GLP-1 secretion from endogenous gastrointestinal cells.

Before describing the present invention in detail, it is to be understood that this invention is not limited to particularly exemplified compounds, compositions or methods, as such may, of course, vary. Thus, although a number of compounds, compositions and methods similar or equivalent to those described herein can be used in the practice of the present invention, the preferred compounds, compositions and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an active agent" includes two or more such agents and the like.

Definitions

The terms "protein", "peptide", "polypeptide" and "polypeptide fragment" as used interchangeably herein, mean, and include amino acid polymers residues of any length. The amino acid polymer can be linear or branched, comprise modified amino acids or amino acid analogs, and it can be interrupted by chemical moieties other than amino acids. The terms "protein", "peptide", "polypeptide" and "polypeptide fragment" also include amino acid polymers that have been modified naturally or synthetically by chemical intervention; by way of example, disulfide bond formation, glycosylation, lipidation, acetylation, phosphorylation, PEGylation or any other manipulation or modification, such as conjugation with a labeling or bioactive component.

The term "endocrine factor" as used herein, means and includes any molecular compound that is produced and secreted by endogenous cells and induces biological activity at a biological tissue site. The term "endocrine factor" thus means and includes, without limitation, glucagon-like peptide-1 (GLP-1), gastric inhibitory polypeptide (GIP), peptide Y-Y (PYY), ghrelin, gastrin, cholecystokinin (CCK), bombesin/gastrin releasing peptide (BBS/GRP), neurotensin (NT), glucagon-like peptide 2 (GLP-2), calcitonin gene-related peptide (CGRP), chromogranin A, enteroglucagon, galanin, leptin, motilin, amylin, neuropeptide Y (NPY), pancreatic polypeptide, substance P, oxyntomodulin, and somatostatin.

The term "agonist" as used herein, means, and includes any molecule which binds to a receptor on a cell, wherein the binding to the receptor can potentially lead to subsequent changes in the cell's functions. When an agonist binds to a sufficient number of receptors, the receptors can activate seminal processes in the cell.

The term "antagonist", as used herein, means and includes a molecule, which binds to a receptor on a cell and inhibits the receptor from activating processes in the cell. The inhibition of the receptor can include competitive binding against agonists (when an antagonist is bound, agonists cannot bind to the receptor) and allosteric effects (when the antagonist binds, agonists can still bind the receptor, but cannot activate the receptor).

The term "olfactory receptor (OR)" as used herein, means and includes an olfactory receptor that is a seminal component of the chemosensory organs responsible for olfaction. The term "olfactory receptor" as used herein, also means, and includes, trace amine associated receptors, vomeronasal receptors, formyl peptide receptors, membrane guanylyl cyclase, subtype GC-D receptors; and G-protein coupled receptors, such as G-protein coupled taste receptors. Olfactory receptors can also include hybrid receptors synthesized from the above-noted olfactory receptors.

The term "ectopic olfactory receptor", as used herein, means and includes an olfactory receptor that is present in organs, tissue, and/or cells that is a seminal component of physiological processes outside of olfaction and, in some instances, indirectly involved with olfactory-mediated processes.

The term "free fatty acid receptor", as used herein, means and includes a transmembrane cell surface receptor that is adapted and configured to bind to fatty acids and induce cell signaling processes in response to the binding of the fatty acids.

The term "transient receptor potential ion channel", as used herein, means and includes a transmembrane ion channel that is adapted and configured to modulate ion entry into an endogenous cell, such as $Ca^{2+}$ entry, and, thereby, induce cell signaling process when a compound or ligand binds to the ion channel.

The term "compound", as used herein, means and includes any composition of matter comprising two or more chemical elements. According to the invention, in some instances, the terms "compound" and "ligand" are synonymous and used interchangeably herein.

The term "compound" thus means and includes, without limitation, 3-methylpentanoic acid, pentanoic acid, pentanol, 4-methylnonanoic acid, eugenol, farnesol, farnesyl thiosalicylic acid, acrolein, formalin, hydrogen peroxide, coumarin, dicyclohexyl disulfide, nonanoic acid, octanioc acid, 2-nonanoic acid, butyric acid, heptanoic acid, decanoic acid, tetradecanoic acid, trans-2-decenoic acid, tridecanoic acid, undecanoic acid, methyl eugenol, methyl salicylate, (+)-menthol, eugenyl acetate, 2,4-dinitrotoluene, 4-hydroxynonenal, hexanoic acid, 2-ethylhexanoic acid, 2-ethyl-3,5-dimethylpyrazine, pyrazine, dimethyl disulfide, methyl furfuryl disulfide, propanal, butyl butyryl lactate, isovaleric acid, propionic acid, 4-methylpentanoic acid, methanoic acid, octanoic acid, octanal, coumarin, helional, lilial, β-ionone, androstenone, androstadienone, caramel furanone, 3-phenyl propyl propionate, ethyl vanillin, 2-ethyl-fencol, N-amyl acetate, eugenol acetate, sandalwood, S-(−)-citronellol, (−)-citronellol, hydroxycitronellal, citral, S-(−)-citronellal, (+)-carvine, (−) carvone, (+) carvone, linalool, bourgeonal, acetophenone, amyl butyrate, nonanethiol, allyl phenyl acetate, N-amyl acetate, muscone, isoeugenol, eugenol methyl ether, heptanol, hexanol, hexyl acetate, 1-hexanol, 1-heptanol, 2-heptanone, octanol, 1-octanol, celery ketone, anis aldehyde, vanillin, guaiacol, hydroxymethylpentylcyclohexenecarboxaldehyde (lyral), allyl phenylacetate, allyl isothiocyanate, benzyl acetate, 3,4-hexanedione, cis-3-hexen-1-ol, quinoline, ethyl heptanoate, methyl octanoate, nonanal, 1-nonanol, 2-nonanol, 3-octanone, 3-nonanone, decyl aldehyde, (E)-non-2-enal 2-ethyl-3,5-dimethylpyrazine 3-methylbut-2-ene-1-thiol, (2E,6Z)-nona-2,6-dienalcitral, ethyl octanoate, p-mentha-8-thiol-3-one, β-myrcene, γ-decalactone, (S)-(+)-carvone, dihydrojasmone, cinnamaldehyde, spearmint, coffee difuran, quinoline, butyl anthranilate 2,2-dithiodimethylenedifuran, ethyl hexanoate, limonene, α-terpineol, eugenol (3E,5Z)-undeca-1,3,5-triene, long-chain free fatty acids (e.g., palmitic acid and stearic acid), medium-chain free fatty acids (e.g., caproic acid (C6:0), caprylic acid (C8:0), capric acid (C10:0), and lauric acid (C12:0)), and omega-3 polyunsaturated fatty acids (e.g., alpha-linoleic acid, docosahexaenoic acid, and eicosatetraenoic acid).

The term "compound" also means and includes any composition of matter included in the Food and Drug Administration's (FDA's) generally recognized as safe (GRAS) database.

The terms "composition", "formulation", "olfactory composition" and "olfactory formulation", as used interchangeably herein, mean and include any compound or combination of compounds that can interact with and modulate at least one olfactory receptor and/or ectopic olfactory receptor and/or free fatty acid receptor and/or transient receptor potential ion channel.

The terms "olfaction" and "olfactory reception" as used interchangeably herein, mean and include the interaction of a composition (or formulation) with an olfactory receptor coupled to a cell signaling pathway. The composition can also be defined as an "odorant" and may be airborne (i.e., volatile) and/or in solution.

The terms "express" and "expression" as used interchangeably herein, mean, and include the production of a protein product from the genetic information contained within a nucleic acid sequence.

The term "upregulation", as used herein, means, and includes the increased production of a protein product from the genetic information contained within a nucleic acid sequence.

The term "downregulation", as used herein, means, and includes the decreased production of a protein product from the genetic information contained within a nucleic acid sequence.

The terms "delivery" and "administration" are used interchangeably herein, and mean and include providing a composition (or formulation), through any method appropriate to deliver the composition (or formulation) to a subject. According to the invention, such administration means includes, without limitation, oral, sublingual, inhalation, intranasal, epidural, intracerebral, transdermal, topical, and injection administration means.

The term "$EC_{50}$", as used herein, means, and includes the concentration of a substance (e.g., a compound or a drug), which, after delivery to a subject, induces at least 50% activation or enhancement of a biological process.

In some embodiments, the term "$EC_{50}$" refers to the concentration of agonist which, after delivery to a subject, induces a response halfway between the baseline and maximum response in an in vitro assay.

In some embodiments, the term "$EC_{50}$" refers to the concentration of a modulator (e.g., an agonist) which, after delivery to a subject, induces at least 50% activation of a receptor type, by way of example, an ectopic olfactory receptor.

The term "$IC_{50}$", as used herein, means, and includes the concentration of a substance (e.g., a compound or a drug), which, after delivery, inhibits or attenuates at least 50% of a biological process.

In some embodiments, the term "$IC_{50}$" refers to the concentration of a modulator (e.g., an antagonist or inhibitor), which, after delivery, inhibits or attenuates at least 50% of receptor activity, e.g., at least 50% of an ectopic olfactory receptor activity.

The term "comprise" and variations of the term, such as "comprising" and "comprises", means "including, but not limited to" and is not intended to exclude, for example, other compounds, ligands or method steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention.

As indicated above, the present invention is directed to compositions and methods for treating diabetes mellitus and obesity by modulating receptor activity.

As discussed above, various entities have developed GLP-1 analogs that mimic endogenous GLP-1 alone, and dual GLP-1/GIP analogs that mimic both endogenous GLP-1 and GIP in combination.

As also discussed above, the GLP-1 analogs activate the GLP-1 receptor on pancreatic β-cells and the dual GLP-1/GIP analogs activate both GLP-1 receptor and GIP receptor on pancreatic β-cells to modulate insulin secretion by the pancreas.

Although the GLP-1 analogs and dual GLP-1/GIP analogs can effectively modulate insulin secretion, as also discussed in detail above, there are several drawbacks and disadvantages associated with administration of GLP-1 analogs and dual GLP-1/GIP analogs to patients, including, a high risk of hypoglycemia, adverse side effects, and high costs.

As discussed in detail below, Applicant has developed compositions that directly and effectively modulate production of endogenous GLP-1 and GIP in vivo, which overcome the drawbacks and disadvantages associated with GLP-1 analogs that merely mimic endogenous GLP-1, and dual GLP-1/GIP analogs that merely mimic endogenous GLP-1 and GIP.

Although the compositions of the invention are described in connection with the treatment of endocrine diseases and disorders; more particularly, the treatment of type-2 diabetes mellitus, and underlying causes thereof; specifically, obesity, use of the compositions is not limited solely to the treatment of endocrine diseases and disorders, and underlying causes thereof. As will readily appreciated by one having ordinary skill in the art, the compositions can also be employed to effectively treat additional diseases and/or disorders, including, without limitation, cardiovascular diseases and disorders, reproductive diseases and disorders, immune diseases and disorders, etc.

As discussed in detail below, in preferred embodiment, the compositions of the invention comprise at least one compound or ligand that is adapted to bind to and activate at least one receptor, e.g., an ectopic olfactory receptor and/or free fatty acid receptor and/or transient receptor potential ion channel, whereby insulin secretion is increased in vivo, and appetite is suppressed.

According to the invention, suitable compounds and ligands (also referred to herein as "receptor activating compounds and ligands") include, without limitation, 3-methylpentanoic acid, pentanoic acid, pentanol, 4-methylnonanoic acid, eugenol, farnesol, farnesyl thiosalicylic acid, acrolein, formalin, hydrogen peroxide, coumarin, dicyclohexyl disulfide, nonanoic acid, octanioic acid, 2-nonanoic acid, butyric acid, heptanoic acid, decanoic acid, tetradecanoic acid, trans-2-decenoic acid, tridecanoic acid, undecanoic acid, methyl eugenol, methyl salicylate, (+)-menthol, eugenyl acetate, 2,4-dinitrotoluene, 4-hydroxynonenal, hexanoic acid, 2-ethylhexanoic acid, 2-ethyl-3,5-dimethylpyrazine, pyrazine, dimethyl disulfide, methyl furfuryl disulfide, propanal, butyl butyryl lactate, isovaleric acid, propionic acid, 4-methylpentanoic acid, methanoic acid, octanoic acid, octanal, coumarin, helional, lilial, β-ionone, androstenone, androstadienone, caramel furanone, 3-phenyl propyl propionate, ethyl vanillin, 2-ethyl-fencol, N-amyl acetate, eugenol acetate, sandalwood, S-(−)-citronellol, (−)-citronellol, hydroxycitronellal, citral, S-(−)-citronellal, (+)-carvine, (−) carvone, (+) carvone, linalool, bourgeonal, acetophenone, amyl butyrate, nonanethiol, allyl phenyl acetate, N-amyl acetate, muscone, isoeugenol, eugenol methyl ether, heptanol, hexanol, hexyl acetate, 1-hexanol, 1-heptanol, 2-heptanone, octanol, 1-octanol, celery ketone, anis aldehyde, vanillin, guaiacol, hydroxymethylpentylcyclohexenecarboxaldehyde (lyral), allyl phenylacetate, allyl isothiocyanate, benzyl acetate, 3,4-hexanedione, cis-3-hexen-1-ol, quinoline, ethyl heptanoate, methyl octanoate, nonanal, 1-nonanol, 2-nonanol, 3-octanone, 3-nonanone, decyl aldehyde, (E)-non-2-enal 2-ethyl-3,5-dimethylpyrazine 3-methylbut-2-ene-1-thiol, (2E,6Z)-nona-2,6-dienalcitral, ethyl octanoate, p-mentha-8-thiol-3-one, β-myrcene, γ-decalactone, (S)-(+)-carvone, dihydrojasmone, cinnamaldehyde, spearmint, coffee difuran, quinoline, butyl anthranilate 2,2-dithiodimethylenedifuran, ethyl hexanoate, limonene, α-terpineol, eugenol (3E,5Z)-undeca-1,3,5-triene, long-chain free fatty acids (e.g., palmitic acid and stearic acid), medium-chain free fatty acids (e.g., caproic acid (C6:0), caprylic acid (C8:0), capric acid (C10:0), and lauric acid (C12:0)), and omega-3 polyunsaturated fatty acids (e.g., alpha-linoleic acid, docosahexaenoic acid and eicosatetraenoic acid).

According to the invention, the receptor activating compounds and ligands (and, hence, compositions of the invention formed therefrom) are adapted to bind to and activate one or more of the following receptors: adipose olfactory receptors (e.g., OR51E2, OR2W3, OR51E1, OR2A1/42, OR2A4/7, OR52N4, OR13A1, 047D2, OR10J1, OR1L8, OR2B6, OR4D6, OLFR16, TAS1R3, TAS2R10, TAS2R13, TAS2R14, TAS2R19, TAS2R20, TAS2R31, TAS2R40, TAS2R42, TAS2R5, VN1R1, and VN1R2), adrenal olfactory receptors (e.g., OR51E2, ORW3, OR51E1, OR2A1/42, OR2A4/7, OR52N4, OR13A1, OR5K2, OR3A2, OR2H2, OR7C1, OR2L13, OR1L8, OR2T8, OR10AD1, OR52B6, OR1E1, OR13J1, OR2C1, OR52D1, OR10A2, OR2B6, OR8G5, OR1F12, OR4D6, TAS1R1, TAS1R3, TAS2R10, TAS2R13, TAS2R14, TAS2R19, TAS2R20, TAS2R3, TAS2R30, TAS2R31, TAS2R4, TAS2R42, TAS2R5, TAS2R50, TAS2R9, and VN1R1), central nervous system (CNS) olfactory receptors (e.g., OR51E2, OR2W3, OR4N4, OR51E1, OR52N4, OR13A1, OR5K2, OR7D2, OR3A2, OR2V1, OR2H2, OR7C1, OR2L13, OR1L8, OR2T8, OR10AD1, OR3A3, OR2K2, OR13J1, OR2C1, OR7A5, OR10A2, OR1F12, TAAR3, TAAR5, TAAR6. TAS1R1, TAS1R3, TAS2R1, TAS2R10, TAS2R13, TAS2R14, TAS2R19, TAS2R20, TAS2R3, TAS2R30, TAS2R31, TAS2R39, TAS2R4, TAS2R40, TAS2R42, TAS2R46, TAS2R5, TAS2R50, TAS2R7, TAS2R8, TAS2R9, VN1R1, VN1R2, and VN1R5), dopaminergic neuron olfactory receptors (e.g., OR51E1, OR51E2, and OR2J3), mammary olfactory receptors (e.g., OR51E2, OR51E1, OR2A1/42, OR2A4/7, OR52N4, OR5K2, OR3A2, OR2T8, OR10AD1, OR3A3, OR2K2, OR1E1, OR2C1, OR2C3, OR8D1, OR7A5, OR10A2, TAS1R1, TAS1R3, TAS2R10, TAS2R13, TAS2R14, TAS2R19, TAS2R20, TAS2R31, TAS2R4, TAS2R5, and VN1R1), cardiovascular olfactory receptors (e.g., OR51E2, OR51E1, OR52N4, OR13A1, OR2H2, OR10AD1, OR3A3, OR52B6, OR2K2, OR8G5, OR4D6, TAS1R1, TAS1R3, TAS2R10, TAS2R13, TAS2R14, TAS2R19, TAS2R20, TAS2R3, TAS2R30, TAS2R31, TAS2R4, TAS2R43, TAS2R46, TAS2R5, TAS2R50, TAS2R7, and VN1R1), renal olfactory receptors (e.g., OR51E2, OR51E1, OR2A1/42, OR2A4/7, OR5K2, OR1L8, OR10A2, OR1F12, TAS1R1, TAS1R3, TAS2R1, TAS2R10, TAS2R14, TAS2R19, TAS2R20, TAS2R3, TAS2R30, TAS2R31, TAS2R4, TAS2R42, TAS2R43, TAS2R5, TAS2R50, and VN1R1), hepatic olfactory receptors (e.g., OR2W3, OR51E1, OR2A1/42, OR2A4/7, OR7D2, OR1L8, OR2T8. TAS1R3, TAS2R14, TAS2R14, TAS2R20, TAS2R30, TAS2R30, TAS2R40, TAS2R5, VN1R1, and VN1R2), lymphatic olfactory receptors (e.g., OR51E2, OR51E1, OR2W3, OR2A1/42, OR2A4/7, OR52N4, OR13A1, OR5K2, OR7D2, OR3A2, OR2H2, OR3A3, OR2B6, OR52B6, TAS1R3, TAS2R14, TAS2R19, TAS2R20, TAS2R31, TAS2R4, TAS2R5, TAS2R40, TAS2R50, TAS2R43, TAS2R5, and VN1R1), ovarian olfactory receptors (e.g., OR51E2, OR2W3, OR4N4, OR51E1, OR2A1/42, OR2A4/7, OR52N4, OR5K2, OR3A2, OR2V1, OR2H2, OR2L13, OR1L8, OR10AD1, OR3A3, OR52B6, OR13J1, OR2C1, OR52D1, OR51B5, OR1F12, TAS1R1, TAS1R3, TAS2R1, TAS2R10, TAS2R13, TAS2R14, TAS2R19, TAS2R20, TAS2R3, TAS2R31, TAS2R4, TAS2R42, TAS2R43, TAS2R5, TAS2R50, TAS2R60, TAS2R7, VN1R1, and VN1R2), prostate olfactory receptors (e.g., OR51E2, OR2W3, OR51E1, OR2A1/42, OR2A4/7, OR52N4, OR13A1, OR5K2, OR2H2, OR7C1, OR1E1, OR13J1, OR51B5, TAS1R3, TAS2R14, TAS2R19, TAS2R20, TAS2R43, TAS2R46, TAS2R5, and VN1R1), dermal olfactory receptors (e.g., OR2AT4), testicular olfactory receptors (e.g., OR4N4, OR6F1, OR2H1, OR51E2, OR2W3, OR4N4, OR51E1, OR2A1/42, OR2A4/7, OR52N4, OR7D2, OR3A2, OR2V1, OR2H2, OR7C1, OR10J1, OR1L8, OR1C1, OR2H1, OR10AD1, OR3A3, OR13C3, OR2K2, OR1E1, OR2C1, OR2K2, OR1E1, OR2C1, OR2C3, OR8D1, OR52D1, OR7A5, OR10A2, OR2B6, OR7E24, OR6F1, OR8G5, OR51B5, OR1F12, TAS1R1, TAS1R3, TAS2R1, TAS2R14, TAS2R19, TAS2R20, TAS2R3, TAS2R31, TAS2R4, TAS2R43, TAS2R5, TAS2R50 TAS2R60, VN1R1, VN1R2, VN1R3, and VN1R4), hematologic olfactory receptors (e.g., OR2W3, OR2A4/7, OR52N4, OR7D2, OR2L13, OR3A3, OR2C1, OR2C3, OR2B6, TAS1R3, TAS2R14, TAS2R20, TAS2R40, and TAS2R60), trace amine-associated receptors (e.g., TAAR1, TAAR2, TAAR3, TAAR4P, TAAR5, TAAR6, TAAR7P, TAAR8, and TAAR9), gastrointestinal (GI) olfactory receptors (e.g., OR51E2, OR2W3, OR51E1, OR2A1/42, OR2A4/7, OR2C1, OR5K2, OR7D2, OR7C1, OR2L13, OR7A5, OR51B5, TAS1R1, TAS1R3, TAS2R14, TAS2R20, TAS2R4, TAS2R43, TAS2R5, and VN1R1, free fatty acid receptors (e.g., FFAR1 and FFAR4), and transient receptor potential ion channels (e.g., TRPA1).

In some embodiments of the invention, the receptor activating compounds and ligands of the invention referenced above and, hence, compositions of the invention formed therefrom are adapted to bind to and activate combinations of the aforementioned receptors, i.e., multiple receptors.

Olfactory Receptor-Mediated GLP-1 and PYY Secretion

In some embodiments of the invention, the receptor activating compounds and ligands, and compositions of the invention formed therefrom are specifically adapted to bind to and activate at least one olfactory receptor including, without limitation, olfactory receptor family 51 subfamily E member 1 (OR51E1), olfactory receptor family 1 subfamily A member 1 (OR1A1), olfactory receptor family 2 subfamily C member 1 (OR2C1), and olfactory receptor family 10 subfamily J member 5 (OR10J5) (referred to herein as "GLP-1/PYY secretion compositions").

According to the invention, the GLP-1/PYY secretion compositions of the invention, when delivered to a patient or subject, effectuate the following highly effective and, hence, desirable pharmacodynamic activity.

Referring to FIG. 1, in a preferred embodiment, the GLP-1/PYY secretion compositions (denoted "2") of the invention target and bind to ectopic olfactory receptors (ORs) (denoted "4") disposed on enteroendocrine cells (in this instance, enteroendocrine L-cells) and pancreatic α-cells (both denoted "10"). The glucose-induced membrane depolarization of the enteroendocrine and α-cells 10 opens the voltage-dependent $Ca^{2+}$ (VDC) channels (denoted "6") of the enteroendocrine and α-cells 10, and the resulting $Ca^{2+}$ influx triggers vesicular exocytosis and increases secretion of GLP-1 (denoted "8") from the cells.

The secreted GLP-1 binds to and activates GLP-1 receptor proteins on pancreatic β-cells, which, as indicated above, induces secretion of insulin.

The secreted insulin also binds to insulin receptors (IR) of the endogenous hepatic cells to suppress hepatic glucose output by inhibiting adipose lipolysis and, thereby, release of glucose into an individual's bloodstream.

The secreted GLP-1 also binds to and activates GLP-1 receptor proteins on endogenous GI cells, such as islet cells of the pancreas, whereby glucagon release is suppressed. The secreted GLP-1 also suppresses glucagon secretion indirectly via its insulinotropic effect on the pancreatic β-cells, more particularly, the secretion of further suppressors of glucagon secretion by endogenous GI cells, e.g., amylin, zinc, and γ-aminobutyric acid (GABA).

The secreted GLP-1 can also bind to GLP-1 receptor proteins on endogenous brain cells, more specifically, glutamatergic neurons of the hindbrain, which can, and often will, decrease the rate of gastric emptying and acid secretion, and, thereby, reduce appetite.

The binding of GLP-1 to the GLP-1 receptor proteins on endogenous enteroendocrine cells also induces peptide Y-Y (PYY) secretion by the endogenous enteroendocrine cells. PYY then subsequently binds to neuropeptide Y receptors on local central nervous system cells, which activate seminal cell signaling cascades that increase the efficiency of digestion and nutrient absorption after meal consumption to promote satiety and suppress appetite.

The GLP-1/PYY secretion compositions of the invention (and GLP-1/GIP secretion compositions of the invention, discussed below), when delivered to a patient or subject, thus induce GLP-1 and/or PYY secretion in vivo, whereby insulin secretion of the patient is induced, and the appetite of the patient is suppressed.

The GLP-1/PYY secretion compositions of the invention (and GLP-1/GIP secretion compositions of the invention) thus provide an effective means of treating diabetes mellitus, and particularly type-2 diabetes mellitus, and obesity.

In a preferred embodiment, the GLP-1/PYY secretion compositions of the invention comprise at least one of the receptor activating compounds listed below in Table I below.

thus comprise one or more receptor activating compounds and/or ligands that are adapted to modulate the activity of OR51E1, whereby, a conformational change is induced in the molecular structure of OR51E1 (also referred to herein as "OR51E1 modulation compositions").

According to the invention, activation of OR51E1 induces a glucose-induced membrane depolarization of endogenous GI cells, more particularly, L-enteroendocrine and pancreatic α-cells and, thereby, opens the voltage-dependent $Ca^{2+}$ (VDC) channels of the L- and α-cells, and the resulting $Ca^{2+}$ influx triggers vesicular exocytosis and increases secretion of GLP-1.

The secreted GLP-1 binds to and activates GLP-1 receptor proteins on pancreatic β-cells, which, as indicated above, induces secretion of insulin into a subject's blood stream.

TABLE I

| Receptor | Expression Site | Compounds/Ligands | Signaling Pathway | Biological Process |
|---|---|---|---|---|
| OR51E1 | Enteroendocrine L-Cell | Nonanoic Acid Butyl Butyryl Lactate Farnesol 3-Methylpentanoic Acid 4-Methylpentanoic Acid Eugenol Isovaleric Acid | AC3-cAMP | Increased GLP-1 Secretion and Activation |
| | | Nonanoic Acid Pentanol Farnesol 3-Methylpentanoic Acid 4-Methylpentanoic Acid Eugenol Isovaleric Acid | cAMP-Mediated | Increased Peptide Y-Y Secretion and Activation |
| OR1A1 | Enteroendocrine L-Cell | Citronellal Hydroxycitronellal Citral Geraniol | AC3-cAMP | Increased GLP-1 Secretion and Activation |
| | | 3-Methyl-2,4-Nonanedione Estragole Neroli Heptanol Octanol Helional Nonanal | cAMP-Mediated | |
| OR2C1 | Pancreatic β-Cells | Octanoic Acid | PLC-IP$_3$ | Upregulation of Glycerol Kinase Protein |
| | | Eugenol Musk Ketone (+)-Dihydrocarvone | cAMP-Mediated | Upregulation of Glycerol Kinase Protein |
| OR10J5 | Hepatocytes | α-Cedrene Lyral | cAMP-PKA-CREB | Downregulation of Lipogenesis Genes |
| | | Thujopsene | cAMP-PKA-AMPK | |

As indicated above, the GLP-1/PYY secretion compositions of the invention can comprise any combination of the aforementioned receptor activating compounds.

As also indicated above, the GLP-1/PYY secretion compositions of the invention are adapted to modulate activity of at least one of the following olfactory receptors: OR51E1, OR1A1, OR2C1, and OR10J5. Modulation of the noted receptors and the desirable pharmacodynamic activity resulting therefrom is described below.

OR51E1 Modulation

In some embodiments of the invention, the GLP-1/PYY secretion compositions of the invention (and GLP-1/GIP secretion compositions of the invention, discussed below)

The secreted insulin then binds to the insulin receptors (IR) of endogenous cells to effectuate the activation of cell signaling cascades that modulate energy metabolism and decrease blood glucose.

In a preferred embodiment, the activation of OR51E1 effectuates secretion modulation and/or activation of at least one of the aforementioned additional endocrine factors.

According to the invention, the activation of OR51E1 can also effectuate secretion modulation and/or activation of additional endocrine factors, including, without limitation, ghrelin, gastrin, cholecystokinin (CCK), bombesin/gastrin releasing peptide (BBS/GRP), neurotensin (NT), glucagon-like peptide 2 (GLP-2), calcitonin gene-related peptide (CGRP), chromogranin A, enteroglucagon, galanin, leptin, motilin, amylin, neuropeptide Y (NPY), pancreatic polypeptide, substance P, oxyntomodulin, and somatostatin.

As indicated below, in some embodiments, the GLP-1/PYY secretion compositions of the invention comprise a single receptor activating compound or ligand, such as farnesol, which is preferably adapted to bind to and activate OR51E1.

In some embodiments, the GLP-1/PYY secretion compositions of the invention comprise a combination of receptor activating compounds and/or ligands, such as farnesol and eugenol, which are similarly preferably adapted to bind to and activate OR51E1.

According to the invention, the GLP-1/PYY secretion compositions of the invention can comprise any suitable combination of the aforementioned receptor activating compounds including, without limitation, (+)-menthol, 2,4-dinitrotoluene, 2-ethylhexanoic acid, 2-nonanoic acid, 3-methylpentanoic acid, 4-methylnonanoic acid, butyl butyryl lactate, butyric acid, decanoic acid, dimethyl disulfide, eugenol, eugenyl acetate, farnesol, heptanoic acid, hexanoic acid, isovaleric acid, methyl eugenol, methyl furfuryl disulfide, methyl salicylate, nonanoic acid, octanioic acid, pentanoic acid, pentanol, propanal, pyrazine, tetradecanoic acid, trans-2-decenoic acid, tridecanoic acid, and undecanoic acid.

In a preferred embodiment of the invention, the GLP-1/PYY secretion compositions of the invention (and, as discussed below, GLP-1/GIP compositions of the invention) comprise at least one of the following receptor activating compounds, which, as indicated above, are adapted to activate OR51E1, whereby GLP-1 and PYY are secreted and, thereby, insulin secretion is increased in vivo: 3-methylpentanoic acid, farnesol, eugenol, and nonanoic acid. Each of the noted receptor activating compounds and the pharmacodynamic activity induced thereby is summarized below.

3-Methylpentanoic Acid

As is well established, 3-methylpentanoic acid is a methyl-branched fatty acid and a derivative compound of pentanoic acid, which carries a methyl group at position 3. 3-methylpentanoic acid is a known plant metabolite, animal metabolite, fungal metabolite, and flavoring agent (which has a cheesy, pungent, and sour odor).

Applicant has found that when 3-methylpentanoic acid binds to an olfactory receptor, such as OR51E1, the 3-methylpentanoic acid induces a conformational change in the molecular structure of OR51E1 that induces the binding of OR51E1 to $G_{olf/stim}$, thereby, activating cyclic adenosine monophosphate (cAMP), which results in an increase in intracellular cAMP levels.

As shown in FIG. 1, the intracellular cAMP molecules activate the opening of cyclic nucleotide gated channels that allow $Ca^{2+}$ and $Na^+$ to enter an endogenous cell (such as an enteroendocrine cell), which leads to depolarization of the cell and initiation of an action potential. As discussed in detail above, activation of an olfactory receptor, in this instance, OR51E1 induces increased in vivo secretion of GLP-1 and PYY.

The secreted GLP-1 binds to and activates GLP-1 receptor proteins on pancreatic β-cells, which, as indicated above, induces secretion of insulin into a subject's blood stream and the secreted PYY binds to neuropeptide Y receptors on local central nervous system cells, which activates seminal cell signaling cascades that increase the efficiency of digestion and nutrient absorption after meal consumption to promote satiety and suppress appetite.

Farnesol

Farnesol is a 15-carbon organic compound that comprises an acyclic sesquiterpene alcohol typically produced from 5-carbon isoprene compounds in both plants and animals. Farnesol is a compound present in many essential oils, such as citronella, neroli, cyclamen, lemon grass, tuberose, rose, musk, balsam, and tolu, and has a subtle floral odor.

Applicant has found that when farnesol binds to an olfactory receptor, such as OR51E1, the farnesol induces a conformational change in the molecular structure of OR51E1 that is substantially similar to the confirmational change induced by 3-methylpentanoic acid and, thus, also induces increased in vivo secretion of GLP-1 and PYY.

Eugenol

Eugenol is an allyl chain-substituted guaiacol and a member of the allylbenzene class of chemical compounds. Eugenol is a colorless to pale yellow, aromatic oily liquid extracted from certain essential oils, more particularly, from the essential oils of clove, nutmeg, cinnamon, basil, and bay leaf, and has a spicy, clove-like odor.

Applicant has found that when eugenol binds to an olfactory receptor, such as OR51E1, the eugenol induces a conformational change in the molecular structure of OR51E1 that is substantially similar to the confirmational change induced by 3-methylpentanoic acid and, thus, also induces increased in vivo secretion of GLP-1 and PYY.

Nonanoic Acid

Nonanoic acid is an organic nine (9)-carbon fatty acid compound with structural formula $CH_3(CH_2)_7CO_2H$. Nonanoic acid is a colorless, oily liquid with an unpleasant, pungent odor.

Applicant has found that when nonanoic acid binds to an olfactory receptor, such as OR51E1, the nonanoic acid induces a conformational change in the molecular structure of OR51E1 that is substantially similar to the confirmational change induced by 3-methylpentanoic acid and, thus, also induces increased in vivo secretion of GLP-1 and PYY.

As indicated above, in a preferred embodiment, the GLP-1/PYY secretion compositions of the invention (and GLP-1/GIP secretion compositions of the invention) comprise at least one of the following receptor activating compounds/ligands, which, as indicated above, are adapted to activate OR51E1, whereby insulin secretion is increased in vivo: 3-methylpentanoic acid, farnesol, eugenol, and nonanoic acid.

In some embodiments of the invention, the GLP-1/PYY secretion compositions of the invention (and GLP-1/GIP secretion compositions of the invention) comprise 3-methylpentanoic acid, farnesol, eugenol, and nonanoic acid.

According to the invention, the GLP-1/PYY secretion compositions of the invention (and GLP-1/GIP secretion compositions of the invention) can also comprise one or more of the following receptor activating compounds/ligands, which, as indicated above, are similarly adapted to activate OR51E1, whereby GLP-1 and PYY are secreted and, thereby, insulin secretion is increased in vivo: butyl butyryl lactate, isovaleric acid, and 4-methylpentanoic acid.

According to the invention, the $EC_{50}$ values of the noted receptor activating compounds/ligands contained in a GLP-1/PYY secretion composition of the invention (and GLP-1/GIP secretion compositions of the invention) can comprise any $EC_{50}$ values or $EC_{50}$ value ranges in the range of approximately 1.0 nM to approximately 200.0 mM.

Thus, according to the invention, the $EC_{50}$ values of the noted receptor activating compounds/ligands contained in the GLP-1/PYY secretion compositions of the invention (and GLP-1/GIP secretion compositions of the invention) can comprise in the range of approximately 0.001 μM to approximately 100000.0 µM, approximately 0.002 µM to approximately 10000.0 µM, approximately 0.003 µM to approximately 1000.0 µM, approximately 0.005 µM to approximately 750.0 µM, approximately 0.01 µM to approximately 500.0 µM, approximately 0.05 µM to approximately 50.0 µM, approximately 0.05 µM to approximately 100.0 µM, approximately 0.05 µM to approximately 150.0 µM, approximately 0.05 µM to approximately 200.0 µM, approximately 0.05 µM to approximately 250.0 µM, approximately 0.05 µM to approximately 300.0 µM, approximately 0.05 µM to approximately 350.0 µM, approximately 0.05 µM to approximately 400.0 µM, approximately 0.05 µM to approximately 450.0 µM, approximately 0.05 µM to approximately 500.0 µM, approximately 0.1 µM to approximately 50.0 µM, approximately 0.1 µM to approximately 100.0 µM, approximately 0.1 µM to approximately 150.0 µM, approximately 0.1 µM to approximately 200.0 µM, approximately 0.1 µM to approximately 250.0 µM, approximately 0.1 µM to approximately 300.0 µM, approximately 0.1 µM to approximately 350.0 µM, approximately 0.1 µM to approximately 400.0 µM, approximately 0.1 µM to approximately 450.0 µM, approximately 0.1 µM to approximately 500.0 µM, approximately 0.1 µM to approximately 1000.0 µM, approximately 0.1 µM to approximately 1500.0 µM, approximately 0.1 µM to approximately 2000.0 µM, approximately 0.1 µM to approximately 2500.0 µM, approximately 0.1 µM to approximately 3000.0 µM, approximately 0.25 µM to approximately 50.0 µM, approximately 0.25 µM to approximately 100.0 µM, approximately 0.25 µM to approximately 150.0 µM, approximately 0.25 µM to approximately 200.0 µM, approximately 0.25 µM to approximately 250.0 µM, approximately 0.25 µM to approximately 300.0 µM, approximately 0.25 µM to approximately 350.0 µM, approximately 0.25 µM to approximately 400.0 µM, approximately 0.25 µM to approximately 450.0 µM, approximately 0.25 µM to approximately 500.0 µM, approximately 0.5 µM to approximately 300.0 µM, approximately 1.0 µM to approximately 50.0 µM, approximately 1.0 µM to approximately 100.0 µM, approximately 1.0 µM to approximately 150.0 µM, approximately 1.0 µM to approximately 200.0 µM, approximately 1.0 µM to approximately 250.0 µM, approximately 1.0 µM to approximately 300.0 µM, approximately 1.0 µM to approximately 350.0 µM, approximately 1.0 µM to approximately 400.0 µM, approximately 1.0 µM to approximately 450.0 µM, approximately 1.0 µM to approximately 500.0 µM, approximately 2.5 µM to approximately 100.0 µM, approximately 5.0 µM to approximately 75.0 µM, approximately 7.5 µM to approximately 50.0 µM, approximately 10.0 µM to approximately 25.0 µM, and/or any $EC_{50}$ values therebetween.

According to the invention, the $EC_{50}$ values of the noted receptor activating compounds/ligands contained in the GLP-1/PYY secretion compositions of the invention (and GLP-1/GIP secretion compositions of the invention) can also comprise in the range of approximately 0.001 µM to approximately 10.0 µM, approximately 0.005 µM to approximately 7.5 µM, approximately 0.01 µM to approximately 5.0 µM, approximately 0.03 µM to approximately 2.5 µM, approximately 0.05 µM to approximately 1.5 µM, approximately 0.03 µM to approximately 1.0 µM, approximately 0.1 µM to approximately 0.5 µM, and/or any $EC_{50}$ values therebetween.

In some embodiments, the $EC_{50}$ values of the noted receptor activating compounds/ligands contained in the GLP-1/PYY secretion compositions of the invention (and GLP-1/GIP secretion compositions of the invention) comprise at least 0.001 µM, at least 0.002 µM, at least 0.003 µM, at least 0.004 µM, at least 0.005 µM, at least 0.006 µM, at least 0.007 µM, at least 0.008 µM, at least 0.009 µM, at least 0.01 µM, at least 0.02 µM, at least 0.03 µM, at least 0.04 µM, at least 0.05 µM, at least 0.06 µM, at least 0.07 µM, at least 0.08 µM, at least 0.09 µM, at least 0.1 µM, at least 0.2 µM, at least 0.3 µM, at least 0.4 µM, at least 0.5 µM, at least 0.6 µM, at least 0.7 µM, at least 0.8 µM, at least 0.9 µM, at least 1.0 µM, at least 2.0 µM, at least 3.0 µM, at least 4.0 µM, at least 5.0 µM, at least 6.0 µM, at least 7.0 µM, at least 8.0 µM, at least 9.0 µM, at least 10.0 µM, at least 20.0 µM, at least 30.0 µM, at least 40.0 µM, at least 50.0 µM, at least 60.0 µM, at least 70.0 µM, at least 80.0 µM, at least 90.0 µM, at least 100.0 µM, at least 200.0 µM, at least 300.0 µM, at least 400.0 µM, at least 500.0 µM, at least 600.0 µM, at least 700.0 µM, at least 800.0 µM, at least 900.0 µM, or at least 1,000.0 µM.

As indicated above, in a preferred embodiment of the invention, the GLP-1/PYY secretion composition comprises 3-methylpentanoic acid, farnesol, eugenol, and nonanoic acid.

In a preferred embodiment, the $EC_{50}$ value of 3-methylpentanoic acid contained in the GLP-1/PYY secretion composition comprises in the range of approximately 5.0 µM to approximately 50.0 µM, more preferably, in the range of approximately 10.0 µM to approximately 30.0 µM.

In a preferred embodiment, the $EC_{50}$ value of farnesol contained in the GLP-1/PYY secretion composition comprises in the range of approximately 0.1 µM to approximately 10.0 µM, more preferably, in the range of approximately 0.4 µM to approximately 0.5 µM.

In a preferred embodiment, the $EC_{50}$ value of eugenol contained in the GLP-1/PYY secretion composition comprises in the range of approximately 0.05 µM to approximately 500.0 µM, more preferably, in the range of approximately 0.1 µM to approximately 350.0 µM.

In a preferred embodiment, the $EC_{50}$ value of nonanoic acid contained in the GLP-1/PYY secretion composition comprises in the range of approximately 0.05 µM to 0.4 µM, more preferably, in the range of approximately 0.1 µM to approximately 0.2 µM.

OR1A1 Modulation

In some embodiments, the GLP-1/PYY secretion compositions of the invention (and GLP-1/GIP secretion compositions of the invention) comprise one or more receptor activating compounds and/or ligands that are specifically adapted to activate OR1A1 whereby, pharmacodynamic activity similar to that induced via activation of OR51E1 (discussed above) is induced (also referred to herein as "OR1A1 modulation compositions").

According to the invention, the GLP-1/PYY secretion compositions of the invention (and GLP-1/GIP secretion compositions of the invention) can comprise one or more of the following receptor activating compounds, which are adapted to activate OR1A1, whereby insulin secretion is similarly increased in vivo: geraniol, citronellol, 3-methyl-2,4-nonanedione, estragole, neroli, heptanol, octanol, helional, nonanal, hydroxycitronellal and citral.

According to the invention, the $EC_{50}$ value of the above noted receptor; specifically, OR1A1, activating compounds contained in a GLP-1/PYY secretion composition of the invention (and GLP-1/GIP secretion compositions of the invention) can similarly comprise any of the aforementioned $EC_{50}$ value ranges and $EC_{50}$ values therebetween.

In some embodiments, the $EC_{50}$ value of geraniol in the GLP-1/PYY secretion compositions of the invention (and GLP-1/GIP secretion compositions of the invention) comprises in the range of approximately 10.0 µM to approximately 250.0 µM.

In some embodiments, the $EC_{50}$ value of geraniol in the GLP-1/PYY secretion compositions of the invention (and GLP-1/GIP secretion compositions of the invention) comprises an $EC_{50}$ value of approximately 100.0 µM.

OR2C1 Modulation

In some embodiments, the GLP-1/PYY secretion compositions of the invention (and GLP-1/GIP secretion compositions of the invention) comprise one or more receptor activating compounds and/or ligands that are specifically adapted to activate OR2C1 whereby, the following pharmacodynamic activity is induced (referred to hereinafter as "OR2C1 modulation compositions").

Activation of OR2C1 induces $Ca^{2+}$ release from the endoplasmic reticulum of pancreatic β-cells through the phospholipase C-inositol triphosphate-dependent (PLC-IP3) pathway and, thereby, an increased concentration of intracellular $Ca^{2+}$. The increase in intracellular $Ca^{2+}$ then activates the CaMKK/CaMKIV pathway, which induces glucokinase (GK) expression, thereby inducing glucose absorption by endogenous cells and glucose-stimulated insulin secretion (GSIS) from pancreatic islet cells.

The secreted insulin then similarly binds to the insulin receptors (IR) of endogenous cells to effectuate the activation of cell signaling cascades that modulate energy metabolism and decrease blood glucose.

In a preferred embodiment, the activation of OR2C1 similarly effectuates secretion modulation and/or activation of at least one of the aforementioned additional endocrine factors.

According to the invention, the GLP-1/PYY secretion compositions of the invention (and GLP-1/GIP secretion compositions of the invention) can comprise one or more of the following receptor activating compounds/ligands, which are adapted to activate OR2C1, whereby insulin secretion is similarly increased in vivo: octanoic acid, eugenol, musk ketone, and (+)-dihydrocarvone.

According to the invention, the $EC_{50}$ value of the above noted receptor; specifically, OR2C1, activating compounds contained in a GLP-1/PYY secretion composition of the invention (and GLP-1/GIP secretion compositions of the invention) can similarly comprise any of the aforementioned $EC_{50}$ value ranges and $EC_{50}$ values therebetween.

OR10J5 Modulation

In some embodiments of the invention, the GLP-1/PYY secretion compositions of the invention (and GLP-1/GIP secretion compositions of the invention) comprise one or more receptor activating compounds and/or ligands that are specifically adapted to activate OR10J5 whereby, the following pharmacodynamic activity is induced (also referred to herein as "OR10J5 modulation compositions").

Activation of OR10J5 induces downregulation of the seminal lipogenesis associated gene expression, including the expression of C/EBPα, PPARγ, RXR, LXRα, SREBP-1c, ap2, FAS, SCD1, ACC, and mtGPAT genes, and upregulation of mitochondrial and thermogenic gene expression, including the expression of PGC-1α, PRDM16, UCP1, Cytc, Cox4, and Cidea genes through the cAMP/PKA/HSL pathway.

The above noted downregulation of the seminal lipogenesis associated gene expression and upregulation of mitochondrial and thermogenic gene expression modulates lipid metabolism by inhibiting lipogenesis and, thus, reducing lipid accumulation in hepatic cells.

In a preferred embodiment, the activation of OR10J5 similarly effectuates secretion modulation and/or activation of at least one of the aforementioned additional endocrine factors.

According to the invention, the GLP-1/PYY secretion compositions of the invention (and GLP-1/GIP secretion compositions of the invention) can comprise one or more of the following receptor activating compounds/ligands, which are adapted to activate OR10J5, whereby insulin secretion is similarly increased in vivo: α-cedrene, hydroxymethylpentyl-cyclohexenecarboxaldehyde (also referred to as "lyral"), and thujopsene.

According to the invention, the $EC_{50}$ value of the above noted receptor; specifically, OR10J5, activating compounds contained in a GLP-1/PYY secretion composition of the invention (and GLP-1/GIP secretion compositions of the invention) can similarly comprise any of the aforementioned $EC_{50}$ value ranges and $EC_{50}$ values therebetween.

Olfactory Receptor-Mediated and Free Fatty Acid Receptor-Mediated (GIP) Secretion In some embodiments of the invention, the receptor activating compounds and ligands, and compositions of the invention formed therefrom are specifically adapted to bind to and activate at least one receptor that induces GIP secretion in vivo including, without limitation, free fatty acid receptor 1 (FFAR1), free fatty acid receptor 4 (FFAR4), olfactory receptor family 2 subfamily W member 1 (OR2W1), olfactory receptor family 2 subfamily B member 11 (OR2B11), olfactory receptor family 2 subfamily J member 3 (OR2J3), and transient receptor potential cation channel subfamily A member 1 (TRPA1) (referred to herein as "GIP secretion compositions").

According to the invention, the GIP secretion compositions of the invention (and GLP-1/GIP secretion compositions of the invention, discussed below), when delivered to a patient or subject, effectuate the following highly effective and, hence, desirable pharmacodynamic activity.

Figure 2:
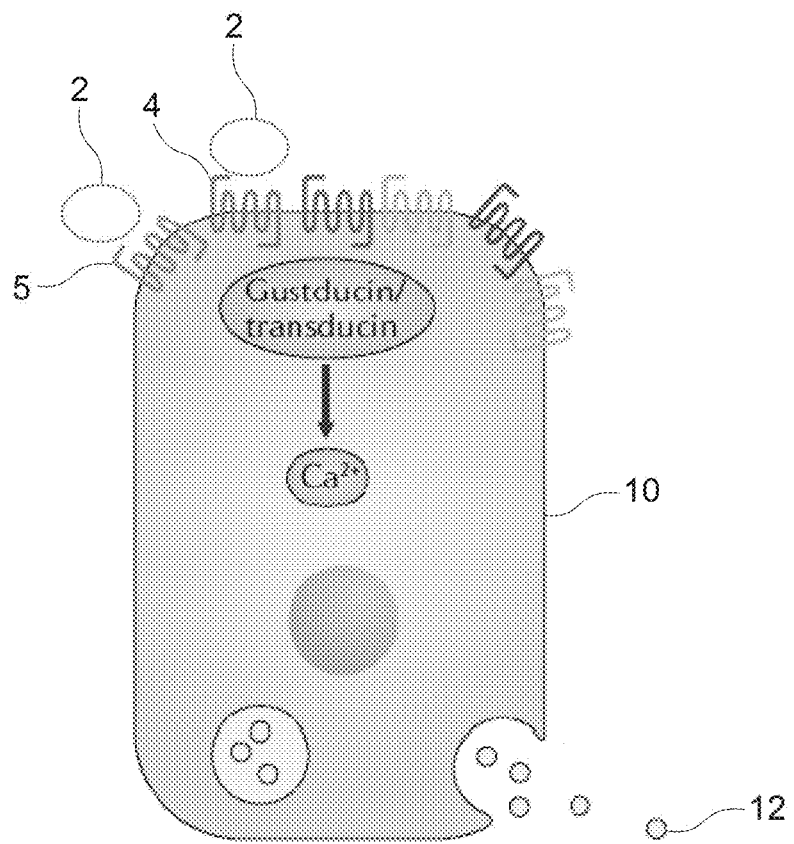
FIG. 2 is a schematic illustration of receptor-mediated activation of GIP secretion from endogenous gastrointestinal cells.

Referring now to FIG. 2, in a preferred embodiment, when a GIP secretion composition of the invention (and GLP-1/GIP secretion composition of the invention) (denoted "2") targets and binds to ectopic olfactory receptors (denoted "4") and free fatty acid receptors (denoted "5") disposed on endogenous cells (in this instance, enteroendocrine cells) (denoted "10"), a gustducin-mediated cell signaling pathway is activated, which induces membrane depolarization of the enteroendocrine cells 10 and opens the voltage-dependent $Ca^{2+}$ (VDC) channels of the enteroendocrine cells 10, wherein the resulting $Ca^{2+}$ influx induces vesicular exocytosis and increased secretion (denoted "12") of GIP from the enteroendocrine cells 10.

The secreted GIP binds to and activates GIP receptor proteins on pancreatic β-cells, which, induces secretion of insulin.

The secreted insulin then binds to the insulin receptors (IR) of endogenous cells to effectuate the activation of cell signaling cascades that modulate energy metabolism and decrease blood glucose.

The secreted insulin also binds to insulin receptors (IR) of the endogenous hepatic cells to suppress hepatic glucose output by inhibiting adipose lipolysis and, thereby, release of glucose into an individual's bloodstream.

The secreted GIP also binds to and activates GIP receptor proteins on endogenous GI cells, such as islet cells of the pancreas, to promote pancreatic β-cell survival and prevent apoptosis of pancreatic β-cells by activating the cAMP response element-binding (CREB) and Akt/PKB pathways, thus, directly, and indirectly maintaining a stable population of insulin-producing pancreatic β-cells in vivo.

The GIP secretion compositions of the invention (and GLP-1/GIP secretion compositions of the invention), when delivered to a patient or subject, thus similarly induce GIP secretion in vivo, whereby insulin secretion of the patient is induced and the appetite of the patient is suppressed.

The GIP secretion compositions of the invention (and GLP-1/GIP secretion compositions of the invention) thus also provide an effective means of treating diabetes mellitus, and particularly type-2 diabetes mellitus, and obesity.

In a preferred embodiment, the GIP secretion compositions of the invention (and GLP-1/GIP secretion compositions of the invention) comprise at least one of the receptor activating compounds/ligands listed below in Table II below.

According to the invention, the activation of FFAR1 and FFAR4 by the receptor activating compounds/ligands induces activation of a gustducin-mediated cell signaling pathway, which induces membrane depolarization of enteroendocrine cells and opens voltage-dependent $Ca^{2+}$ (VDC) channels of the enteroendocrine cells, wherein the resulting $Ca^{2+}$ influx induces increased secretion of GIP from the enteroendocrine cells.

The activation of FFAR1 and/or FFAR4, can, in some instances, also induce activation of $G_{aq/11}$ and β-arrestin signaling pathways and, thereby, stimulate further GIP secretion.

The secreted GIP binds to and activates GIP receptor proteins on pancreatic β-cells, which induces secretion of insulin.

TABLE II

| Receptor | Expression Site | Compounds/Ligands | Signaling Pathway | Biological Process |
|---|---|---|---|---|
| FFAR1 | Enteroendocrine L-Cells | Medium-Chain Free Fatty Acids (e.g., lauric acid (C12:0)) | Gustducin/ Transducin | Increased GIP Secretion and Activation |
| FFAR4 | Enteroendocrine L-Cells Pancreatic δ-Cells | Long-Chain Free Fatty Acids (e.g., stearic acid) Omega-3 Polyunsaturated Fatty Acids (e.g., alpha-linoleic acid, docosahexaenoic acid, and eicosatetraenoic acid) | | Inhibition of Somatostatin to Promote Insulin Secretion |
| OR2W1 | Enteroendocrine L-Cells Adipose Tissue Cells | 2-Heptanone 1-Octanal (-)-Citronellol Hexanal 3-Octanone Hexyl Acetate 1-Hexanol Octanoic Acid 1-Heptanol Allyl Phenylacetate Benzyl Acetate 3,4-Hexanedione Cis-3-Hexen-1-ol | AC3-cAMP | Increased GIP Secretion and Activation |
| OR2B11 | Enteroendocrine L-Cells | 2-Ethyl-3,5-Dimethylpyrazine Coumarin Dicyclohexyl Disulfide Spearmint Coffee Difuran Quinoline Cinnamaldehyde | AC3-cAMP | Increased GIP Secretion and Activation |
| OR2J3 | Enteroendocrine L-Cells | Cis-3-Hexen-1-ol Cinnamaldehyde | AC3-cAMP | Increased GIP Secretion and Activation |
| TRPA1 | Enterochromaffin Cells | Allyl Isothiocyanate Cinnamaldehyde Farnesyl Thiosalicylic Acid Formalin Hydrogen Peroxide 4-Hydroxynonenal Acrolein | $Ca^{2+}$ | Increased GIP Secretion and Activation |

In a preferred embodiment of the invention, the GIP secretion compositions of the invention (and GLP-1/GIP secretion compositions of the invention) comprise at least one of the receptor activating compounds and/or ligands that are set forth in Table II above, which are specifically adapted to activate at least FFAR1 and/or FFAR4.

The secreted insulin then binds to the insulin receptors (IR) of endogenous cells to effectuate the activation of cell signaling cascades that modulate energy metabolism and decrease blood glucose.

The secreted insulin also binds to insulin receptors (IR) of the endogenous hepatic cells to suppress hepatic glucose output by inhibiting adipose lipolysis and, thereby, release of glucose into an individual's bloodstream.

The secreted GIP also binds to and activates GIP receptor proteins on endogenous GI cells, such as islet cells of the pancreas, to promote pancreatic j-cell survival and prevent apoptosis of pancreatic β-cells by activating the cAMP response element-binding (CREB) and Akt/PKB pathways, thus, directly and indirectly maintaining a stable population of insulin-producing pancreatic β-cells in vivo.

In a preferred embodiment, activation of FFAR1 and/or FFAR4, also effectuates secretion modulation and/or activation of at least one of the aforementioned additional endocrine factors.

As indicated above, in a preferred embodiment, the GIP secretion compositions of the invention (and GLP-1/GIP secretion compositions of the invention) comprise one or more receptor activating compounds/ligands, which, as indicated above, are adapted to activate FFAR1 and/or FFAR4.

In a preferred embodiment, the receptor activating compounds/ligands thus comprise a medium-chain free fatty acid, a long-chain free fatty acid, and an omega-3 polyunsaturated fatty acid. Each of the noted receptor activating compounds and the pharmacodynamic activity induced thereby is summarized below.

Medium-Chain Free Fatty Acids

As is well established, a medium-chain free fatty acid is a fatty acid comprising a carboxylic acid head group with a 6-12 carbon aliphatic chain (saturated or unsaturated) with a methyl group on the end of the aliphatic chain. Foods that are rich in medium chain fatty acids include, without limitation, palm kernel oil and coconut oil.

Applicant has found that when a medium-chain free fatty acid binds to a free fatty acid (FFA) receptor, such as FFAR1 or FFAR4, the medium-chain free fatty acid induces a conformational change in the molecular structure of the FFA receptor that induces the intracellular $G_\alpha/G_\beta/G_\gamma$ subunits of the FFA receptor to act as a guanine nucleotide exchange factor and, thus, exchange a guanine diphosphate (GDP) for a guanine triphosphate (GTP), which binds to the $G_\alpha$ subunit of the FFAR1 or FFAR4.

The noted binding of the GTP to the $G_\alpha$ subunit then induces a dissociation of the $G_\alpha/G_\beta/G_\gamma$ subunits of the FFAR1 or FFAR4 into a (i) free $G\alpha$ subunit and a (ii) $G_\beta/G_\gamma$ complex and, thereby, activates seminal downstream cell signaling processes that induce an increase in intracellular cAMP in endogenous cells, such as enteroendocrine cells.

As depicted in FIG. 2, by virtue of the intracellular cAMP level increase, the opening of cyclic nucleotide gated $Ca^{2+}$ channels is induced, which results in increased cellular $Ca^{2+}$ and, thereby, induction of increased secretion of GIP from the endogenous cells.

The secreted GIP binds to and activates GIP receptor proteins on pancreatic β-cells, which, as indicated above, (i) induces secretion of insulin, (ii) promotes pancreatic β-cell survival, and (iii) prevents apoptosis of pancreatic β-cells by activating the cAMP response element-binding (CREB) and Akt/PKB pathways, thus, directly, and indirectly maintaining a stable population of insulin-producing pancreatic β-cells in vivo.

According to the invention, suitable medium-chain free fatty acids comprise, without limitation, lauric acid, caproic acid, caprylic acid and capric acid.

In a preferred embodiment, the medium-chain free fatty acid comprises lauric acid.

Long-Chain Free Fatty Acids

As is well established, a long-chain free fatty acid is a fatty acid comprising a carboxylic acid head group attached to a 12-21 aliphatic carbon chain that can be saturated or unsaturated and includes a methyl group on the terminal carbon.

Applicant has found that when a long-chain free fatty acid binds to an FFA receptor, such as FFAR1 or FFAR4, the long-chain free fatty acid induces a conformational change in the molecular structure of the FFA receptor that is substantially similar to the confirmational change in the molecular structure of an FFA receptor that is induced by a medium-chain free fatty acid and, thus, also induces increased in vivo secretion of GIP.

According to the invention, suitable long-chain free fatty acids comprise, without limitation, palmitic acid and stearic acid.

In a preferred embodiment, the long-chain free fatty acid comprises stearic acid.

Omega-3 Polyunsaturated Fatty Acids

As is well established, an omega-3 polyunsaturated fatty acid is a polyunsaturated fatty acid that comprises a carboxylic acid head group attached to a polyunsaturated aliphatic carbon chain with carbon-carbon double bonds disposed three carbons from the terminal methyl group.

It is well established that several omega-3-fatty acids are essential dietary molecules, which means that the human body either has difficulty making these molecules or cannot make these molecules and, thus, must be supplied in human diets from outside sources.

Applicant has found that when an omega-3 polyunsaturated fatty acid binds to an FFA receptor, such as FFAR1 or FFAR4, the omega-3 polyunsaturated fatty acid fatty acid induces a conformational change in the molecular structure of the FFA receptor that is substantially similar to the confirmational change in the molecular structure of an FFA receptor that is induced by a medium-chain free fatty acid and, thus, also induces increased in vivo secretion of GIP.

According to the invention, suitable omega-3 polyunsaturated acids comprise, without limitation, alpha-linoleic acid, docosahexaenoic acid, and eicosatetraenoic acid.

In a preferred embodiment, the omega-3 polyunsaturated acid comprises alpha-linoleic acid.

According to the invention, the $EC_{50}$ value of the above noted FFA receptor activating compounds contained in a GIP secretion composition of the invention (and, as discussed below, GLP-1/GIP secretion compositions of the invention) can similarly comprise any of the aforementioned $EC_{50}$ value ranges and $EC_{50}$ values therebetween.

As indicated above, according to the invention, the GIP secretion compositions of the invention (and GLP-1/GIP secretion compositions of the invention) can also comprise one or more receptor activating compounds and/or ligands that are specifically adapted to modulate the activity of olfactory receptor family 2 subfamily W member 1 (OR2W1), olfactory receptor family 2 subfamily B member 11 (OR2B11), olfactory receptor family 2 subfamily J member 3 (OR2J3) and transient receptor potential cation channel subfamily A member 1 (TRPA1), whereby GIP secretion in vivo is similarly induced.

Modulation of the noted receptors and the desirable pharmacodynamic activity resulting therefrom is described below.

OR2W1 Modulation

In some embodiments of the invention, the GIP secretion compositions of the invention (and GLP-1/GIP secretion compositions of the invention, thus comprise one or more receptor activating compounds and/or ligands that are adapted to modulate the activity of OR2W1, more particularly, activate OR2W1 whereby, a conformational change is induced in the molecular structure of OR2W1 (also referred to herein as "OR2W1 modulation compositions").

Applicant has found that when a compound/ligand, e.g., 2-heptanone, binds to OR2W1, the compound induces a conformational change in the molecular structure of the OR2W1 that similarly induces the intracellular $G_\alpha/G_\beta/G_\gamma$ subunits of the olfactory receptor to act as a guanine nucleotide exchange factor and, thus, exchange a guanine diphosphate (GDP) for a guanine triphosphate (GTP), which binds to the $G_\alpha$ subunit of the OR2W1.

The noted binding of the GTP to the $G_\alpha$ subunit then induces a dissociation of the $G_\alpha/G_\beta/G_\gamma$ subunits of the OR2W1 into a (i) free $G\alpha$ subunit and a (ii) $G_\beta/G_\gamma$ complex and, thereby, activates seminal downstream cell signaling processes that induce an increase in intracellular cAMP in endogenous cells, such as enteroendocrine cells.

As depicted in FIG. 2, by virtue of the intracellular cAMP level increase, the opening of cyclic nucleotide gated $Ca^{2+}$ channels is induced, which results in increased cellular $Ca^{2+}$ and, thereby, increased induction of secretion of GIP from the endogenous cells.

The secreted similarly GIP binds to and activates GIP receptor proteins on pancreatic β-cells, which, as indicated above, (i) induces secretion of insulin, (ii) promotes pancreatic β-cell survival, and (iii) prevents apoptosis of pancreatic β-cells by activating the cAMP response element-binding (CREB) and Akt/PKB pathways, thus, directly and indirectly maintaining a stable population of insulin-producing pancreatic β-cells in vivo.

In some embodiments, the activation of OR2W1 similarly effectuates secretion modulation and/or activation of at least one of the aforementioned additional endocrine factors.

According to the invention, the GIP secretion compositions of the invention (and GLP-1/GIP secretion compositions of the invention) can comprise one or more of the following receptor activating compounds/ligands, which, as indicated above, are adapted to activate OR2W1, whereby insulin secretion is similarly increased in vivo: 2-heptanone, 1-octanal, (−)-citronellol, hexanal, 3-octanone, hexyl acetate, 1-hexanol, octanoic acid, 1-heptanol, allyl phenylacetate, benzyl acetate, 3,4-hexanedione, and cis-3-hexen-1-ol.

According to the invention, the $EC_{50}$ value of the above noted receptor; specifically, OR2W1, activating compounds contained in a GIP secretion composition of the invention (and, GLP-1/GIP secretion compositions of the invention) can similarly comprise any of the aforementioned $EC_{50}$ value ranges and $EC_{50}$ values therebetween.

OR2B11 Modulation

In some embodiments of the invention, the GIP secretion compositions of the invention (and GLP-1/GIP secretion compositions of the invention) thus comprise one or more receptor activating compounds and/or ligands that are specifically adapted to activate OR2B11 whereby, pharmacodynamic activity similar to that induced via activation of OR2W1 (discussed above) is induced (also referred to herein as "OR2B11 modulation compositions").

According to the invention, the GIP secretion compositions of the invention (and GLP-1/GIP secretion compositions of the invention) can comprise one or more of the following receptor activating compounds/ligands, which are adapted to activate OR2B11, whereby secretion of GIP is similarly induced in vivo: 2-ethyl-3,5-dimethylpyrazine, coumarin, dicyclohexyl disulfide, spearmint, coffee difuran, quinoline, and cinnamaldehyde.

According to the invention, the $EC_{50}$ value of the above noted receptor; specifically, OR2B11, activating compounds contained in a GIP secretion composition of the invention (and, GLP-1/GIP secretion compositions of the invention) can similarly comprise any of the aforementioned $EC_{50}$ value ranges and $EC_{50}$ values therebetween.

OR2J3 Modulation

In some embodiments of the invention, the GIP secretion compositions of the invention (and GLP-1/GIP secretion compositions of the invention) thus comprise one or more receptor activating compounds and/or ligands that are specifically adapted to activate OR2J3 whereby, pharmacodynamic activity similar to that induced via activation of OR2W1 (discussed above) is induced (referred to hereinafter as "OR2J3 modulation compositions").

According to the invention, the GIP secretion compositions of the invention (and GLP-1/GIP secretion compositions of the invention) can thus comprise one or more of the following receptor activating compounds/ligands, which are adapted to activate OR2J3, whereby secretion of GIP is similarly induced in vivo: cis-3-hexen-1-ol and cinnamaldehyde.

According to the invention, the $EC_{50}$ value of the above noted receptor; specifically, OR2J3, activating compounds contained in a GIP secretion composition of the invention (and, GLP-1/GIP secretion compositions of the invention) can similarly comprise any of the aforementioned $EC_{50}$ value ranges and $EC_{50}$ values therebetween.

TRPA1 Modulation

In some embodiments of the invention, the GIP secretion compositions of the invention (and GLP-1/GIP secretion compositions of the invention, thus comprise one or more receptor activating compounds and/or ligands that are adapted to modulate the activity of TRPA1, more particularly, activate TRPA1 whereby, a conformational change is induced in the molecular structure of TRPA1 (also referred to herein as "TRPA1 modulation compositions").

It is believed that when a compound/ligand, e.g., cinnamaldehyde, binds to TRPA1, the compound increases cellular $Ca^{2+}$ and, thereby, increased serotonin (5-HT) secretion from endogenous enterochromaffin cells.

The serotonin secreted from the enterochromaffin cells binds to 5-HT receptors of endogenous gastrointestinal cells and, thereby, induces GIP secretion by the endogenous cells.

According to the invention, the GIP secretion compositions of the invention (and GLP-1/GIP secretion compositions of the invention) can comprise one or more of the following receptor activating compounds/ligands, which are adapted to activate TRPA1, whereby secretion of GIP is similarly induced in vivo: allyl isothiocyanate, cinnamaldehyde, farnesyl thiosalicylic acid, formalin, hydrogen peroxide, 4-hydroxynonenal, and acrolein.

According to the invention, the $EC_{50}$ value of the above noted receptor; specifically, TRPA1, activating compounds contained in a GIP secretion composition of the invention (and, GLP-1/GIP secretion compositions of the invention) can similarly comprise any of the aforementioned $EC_{50}$ value ranges and $EC_{50}$ values therebetween.

Preferably, the GIP secretion compositions of the invention (and GLP-1/GIP secretion compositions of the invention) are formulated and adapted to activate a plurality of olfactory receptors, e.g., OR51E1, OR2C1, and OR2W1, and a plurality of free fatty acid receptors, e.g., FFAR1 and FFAR4, and, in some instances, a plurality of transient receptor potential ion channels (e.g., TRPA1).

According to the invention, the GIP secretion compositions of the invention and, as discussed below, GLP-1/GIP secretion compositions of the invention, are adapted to induce at least 50% activation of at least FFAR1 and/or FFAR4 and/or OR2W1 and/or OR2B11 and/or OR2J3 and/or TRPA1 in vivo when delivered to a patient.

In a preferred embodiment, the GIP secretion compositions of the invention (and GLP-1/GIP secretion compositions of the invention) are adapted to induce at least 50% activation of FFAR1 or FFAR4 in vivo when delivered to a patient.

Concomitant Modulation of GLP-1 and GIP Secretion

In some embodiments of the invention, the receptor activating compounds and ligands, and compositions of the invention formed therefrom are specifically adapted to bind to and activate at least one receptor that induces GLP-1 secretion and at least one receptor that induces GIP secretion in vivo, including, without limitation, OR51E1, OR1A1, OR2C1, OR10J5, OR2W1, OR2B11, OR2J3, FFAR1, FFAR4 and TRPA1, whereby GLP-1 and GIP is induced in vivo (referred to herein as "GLP-1/GIP secretion compositions").

According to the invention, GLP-1/GIP secretion compositions can thus comprise one or more of the receptor activating compounds/ligands set forth in Tables I and II and discussed above.

As indicated above, according to the invention, the $EC_{50}$ value of the receptor activating compounds/ligands contained in a GLP-1/GIP secretion composition of the invention can comprise any of the aforementioned $EC_{50}$ value ranges and $EC_{50}$ values therebetween.

In some embodiments, the GLP-1/GIP secretion compositions of the invention are specifically formulated and adapted to activate at least OR51E1 and FFAR1.

In some embodiments, the GLP-1/GIP secretion compositions of the invention thus comprise farnesol and at least one omega-3 polyunsaturated fatty acid; preferably, docosahexaenoic acid.

In a preferred embodiment, the $EC_{50}$ value of farnesol contained in the GLP-1/GIP secretion composition comprises in the range of approximately 0.1 µM to approximately 10.0 µM, more preferably, in the range of approximately 0.4 µM to approximately 0.5 µM.

In a preferred embodiment, the $EC_{50}$ value of docosahexaenoic acid contained in the GLP-1/GIP secretion composition comprises in the range of approximately 0.05 µM to approximately 0.4 µM, more preferably, in the range of approximately 0.01 µM to approximately 0.02 µM.

In one preferred embodiment of the invention, the GLP-1/GIP secretion compositions of the invention comprise 3-methylpentanoic acid, farnesol, eugenol, nonanoic acid, stearic acid, lauric acid, alpha-linoleic acid, docosahexaenoic acid and eicosatetraenoic acid.

In a preferred embodiment, the $EC_{50}$ value of 3-methylpentanoic acid contained in the GLP-1/GIP secretion composition comprises in the range of approximately 5.0 µM to approximately 50.0 µM, more preferably, in the range of approximately 10.0 µM to approximately 30.0 µM.

In a preferred embodiment, the $EC_{50}$ value of farnesol contained in the GLP-1/GIP secretion composition similarly comprises in the range of approximately 0.1 µM to approximately 10.0 µM, more preferably, in the range of approximately 0.4 µM to approximately 0.5 µM.

In a preferred embodiment, the $EC_{50}$ value of eugenol contained in the GLP-1/GIP secretion composition comprises in the range of approximately 0.05 µM to approximately 500.0 µM, more preferably, in the range of approximately 0.1 µM to approximately 350.0 µM.

In a preferred embodiment, the $EC_{50}$ value of nonanoic acid contained in the GLP-1/GIP secretion composition comprises in the range of approximately 0.05 µM to approximately 0.4 µM, more preferably, in the range of approximately 0.1 µM to approximately 0.2 µM.

In a preferred embodiment, the $EC_{50}$ value of stearic acid contained in the GLP-1/GIP secretion composition comprises in the range of approximately 0.05 µM to approximately 0.5 µM, more preferably, in the range of approximately 0.1 µM to approximately 0.2 µM.

In a preferred embodiment, the $EC_{50}$ value of lauric acid contained in the GLP-1/GIP secretion composition comprises in the range of approximately 0.05 µM to approximately 75.0 µM, more preferably, in the range of approximately 0.05 µM to approximately 50.0 µM.

In a preferred embodiment, the $EC_{50}$ value of alpha-linoleic acid contained in the GLP-1/GIP secretion composition comprises in the range of approximately 0.01 µM to approximately 0.3 µM, more preferably, in the range of approximately 0.01 µM to approximately 0.02 µM.

In a preferred embodiment, the $EC_{50}$ value of docosahexaenoic acid contained in the GLP-1/GIP secretion composition similarly comprises in the range of approximately 0.05 µM to approximately 0.4 µM, more preferably, in the range of approximately 0.01 µM to approximately 0.02 µM.

In a preferred embodiment, the $EC_{50}$ value of eicosatetraenoic acid contained in the GLP-1/GIP secretion composition comprises in the range of approximately 0.01 µM to approximately 0.4 µM, more preferably, in the range of approximately 0.01 µM to approximately 0.02 µM.

In a preferred embodiment, the GLP-1/GIP secretion compositions of the invention are adapted to induce at least 50% activation of at least OR51E1 and/or OR1A1 and/or OR2C1 and/or OR10J5 and/or FFAR1 and/or FFAR4 and/or OR2W1 and/or OR2B11 and/or OR2J3 and/or TRPA1 in vivo when delivered to a patient.

As indicated above, in a preferred embodiment, the GLP-1/GIP secretion compositions of the invention are adapted to induce at least 50% activation of multiple receptors; particularly, OR51E1 and FFAR1 or FFAR4.

According to the invention, modulating the activity of multiple receptors, e.g., olfactory receptors and/or free fatty acid receptors and/or transient receptor potential ion channels, as described herein, results in elevated endocrine factor levels.

In some embodiments, modulating the activity of multiple receptors, e.g., olfactory receptors and/or free fatty acid receptors and/or transient receptor potential ion channels, as described herein, results in synergistically elevated endocrine factor levels.

In some embodiments, modulating the activity of multiple receptors, e.g., olfactory receptors and/or free fatty acid receptors and/or transient receptor potential ion channels, as described herein, results in elevated endocrine factor secretion.

In some embodiments, modulating the activity of multiple receptors, e.g., olfactory receptors and/or free fatty acid receptors and/or transient receptor potential ion channels, as described herein, results in synergistically elevated endocrine factor secretion.

In some embodiments, modulating the activity of multiple receptors, e.g., olfactory receptors and/or free fatty acid receptors and/or transient receptor potential ion channels, as described herein, results in endocrine factor secretion higher than endocrine factor secretion induced when modulating the activity of any single receptor alone.

In some embodiments, modulating the activity of multiple receptors, e.g., olfactory receptors and/or free fatty acid receptors and/or transient receptor potential ion channels, as described herein, induces a beneficial biological response, including, by way of example, increased insulin secretion, lower food consumption, increased body mass reduction, increased cAMP levels, increased nutrient absorption, increased small intestinal length, increased small intestinal weight, increased villus height, or increased villus height/crypt depth ratio than when modulating the activity of any single receptor alone.

In some embodiments, the compositions of the invention further comprise a physiologically suitable (or acceptable) carrier (also referred to herein as a physiologically suitable (or acceptable) excipient, or physiologically suitable (or acceptable) excipient selected based on a chosen route of administration, e.g., oral administration, and standard pharmaceutical practice.

According to the invention, suitable aqueous and non-aqueous carriers that can be employed in the compositions of the invention include water, ethanol, polyols (such as glycerol, glycerin-based water, propylene glycol, polyethylene glycol, and the like), and suitable mixtures thereof; vegetable oils, such as olive oil; buffers, such as neutral buffered saline, phosphate buffered saline and the like; carbohydrates, such as glucose, mannose, sucrose, and dextran, mannitol; proteins; polypeptides, and amino acids, such as glycine; antioxidants; chelating agents such as ethylenediaminetetraacetic acid (EDTA) or glutathione; adjuvants (e.g., aluminum hydroxide); and injectable organic esters, such as ethyl oleate and cyclodextrins.

According to the invention, the compositions can be manufactured by means of conventional mixing, dissolving, granulating, dragee-making, levigating, emulsifying, encapsulating, entrapping, and lyophilizing processes. The manufactured compositions can take the form of solutions, suspensions, emulsion, tablets, pills, pellets, capsules, capsules containing liquids, powders, sustained-release formulations, suppositories, emulsions, aerosols, sprays, suspensions, and other forms suitable for administration to a patient.

In some embodiments, proper fluidity of a composition is maintained via coating materials, such as lecithin.

According to the invention, the compositions of the invention can be formulated into any known form suitable for parenteral administration, e.g., injection or infusion. Alternatively, the compositions can be formulated for oral administration, nasal or other mucosal tissue administration, or administration as a suppository (e.g., for small molecules). The compositions can also comprise formulation additives, such as suspending agents, preservatives, stabilizers and/or dispersants, and preservation agents.

According to the invention, the compositions can thus be administered to a patient via any suitable method, including, without limitation, oral, sublingual, inhalation, intranasal, epidural, intracerebral, transdermal, topical, and injection administration means.

The compositions of the invention can also be administered to a patient via intraarterial, subcutaneous, intradermal, intratumoral, intranodal, intramedular, intramuscular, intranasally, and intraperitoneal means.

According to the invention, the compositions of the invention can also be incorporated into various ingestible fluids, such as flavored waters and coffee.

According to the invention, the compositions of the invention can also be incorporated into a food item, such as a cracker, and/or a nutritional supplement or supplemental food item, such as protein bar.

According to the invention, the compositions of the invention can be administered at any of the following dosage ranges and dosages therebetween:

(i) about 50.0 mg/kg to about 10.0 g/kg;
(ii) about 100.0 g/kg to about 50.0 mg/kg;
(iii) about 1.0 mg/kg to about 50.0 mg/kg; and
(iv) about 5.0 mg/kg to about 25.0 mg/kg.

In some embodiments, the compositions are administered at one of the following dosage ranges (and/or dosages therebetween) over time:

(i) from about 1.0 mg to about 5.0 g per day;
(ii) from about 10.0 mg to about 4.0 g per day; and
(iii) from about 20.0 mg to about 2.0 g per day.

According to the invention, compositions can also be administered multiple times per day at these dosages.

According to the invention, the noted dosages and delivery protocols are sufficient to induce sustained (i.e., extended periods) of GLP-1, PYY and/or GIP secretion in vivo.

In some embodiments of the invention, there is thus provided a composition for treating an endocrine disorder of a patient; particularly, type-2 diabetes, comprising a GLP-1/PYY secretion composition comprising a delivery medium and at least one receptor activating compound selected from the group comprising 3-methylpentanoic acid, farnesol, eugenol, and nonanoic acid, the GLP-1/PYY secretion composition adapted to effectuate GLP-1 and PYY secretion, and, thereby, increased insulin secretion in vivo.

In some embodiments, the receptor activating compound comprises 3-methylpentanoic acid, wherein the 3-methylpentanoic acid preferably comprises an $EC_{50}$ value in the range of approximately 5.0 µM to approximately 50.0 µM.

In some embodiments, the receptor activating compound comprises farnesol, wherein the farnesol preferably comprises an $EC_{50}$ value in the range of approximately 0.1 µM to approximately 10.0 µM.

In some embodiments, the receptor activating compound comprises eugenol, wherein the eugenol preferably comprises an $EC_{50}$ value in the range of approximately 0.1 µM to approximately 350.0 µM.

In some embodiments, the receptor activating compound comprises nonanoic acid, wherein the nonanoic acid preferably comprises an $EC_{50}$ value in the range of approximately 0.05 µM to approximately 0.4 µM.

In some embodiments of the invention, the GLP-1/PYY secretion compositions comprise (i) a delivery medium, (ii) at least a first receptor activating compound and (iii) at least a second receptor activating compound, the first receptor activating compound being adapted to bind to and activate at least one first receptor selected from the group comprising olfactory receptor OR51E1, olfactory receptor OR1A1, olfactory receptor OR2C1, and olfactory receptor OR10J5, the second receptor activating compound adapted to bind to and activate at least one second receptor selected from the group comprising free fatty acid receptor FFAR1, free fatty acid receptor FFAR4, olfactory receptor OR2W1, olfactory receptor OR2B11, olfactory receptor OR2J3, and transient receptor TRPA1, the GLP-1/GIP secretion composition similarly adapted to effectuate at least GLP-1 and GIP secretion, and, thereby, increased insulin secretion in vivo.

In a preferred embodiment, the first receptor activating compound comprises 3-methylpentanoic acid, farnesol, eugenol or nonanoic acid.

In some embodiments of the invention, the first receptor activating compound comprises 3-methylpentanoic acid.

In a preferred embodiment, the $EC_{50}$ value of 3-methylpentanoic acid in the GLP-1/GIP secretion composition comprises in the range of approximately 5.0 µM to approximately 50.0 µM.

In some embodiments of the invention, the first receptor activating compound comprises farnesol.

In a preferred embodiment, the $EC_{50}$ value of farnesol in the GLP-1/GIP secretion composition comprises in the range of approximately 0.1 µM to approximately 10.0 µM.

In some embodiments of the invention, the first receptor activating compound comprises eugenol.

In a preferred embodiment, the $EC_{50}$ value of eugenol in the GLP-1/GIP secretion composition comprises in the range of approximately 0.1 µM to approximately 350.0 µM.

In some embodiments of the invention, the first receptor activating compound comprises nonanoic acid.

In a preferred embodiment, the $EC_{50}$ value of nonanoic acid in the GLP-1/GIP secretion composition comprises in the range of approximately 0.05 µM to approximately 0.4 µM.

In a preferred embodiment, the second receptor activating compound comprises a medium-chain free fatty acid, a long-chain free fatty acid or an omega-3 polyunsaturated fatty acid.

In some embodiments, the medium-chain free fatty acid comprises lauric acid.

In a preferred embodiment, the $EC_{50}$ value of lauric acid in the GLP-1/GIP secretion composition comprises in the range of approximately 0.05 µM to approximately 50.0 µM.

In some embodiments, the long-chain free fatty acid comprises stearic acid.

In a preferred embodiment, the $EC_{50}$ value of stearic acid in the GLP-1/GIP secretion composition comprises in the range of approximately 0.05 µM to approximately 0.5 µM.

In some embodiments, the omega-3 polyunsaturated fatty acid comprises alpha-linoleic acid.

In a preferred embodiment, the $EC_{50}$ value of alpha-linoleic acid in the GLP-1/GIP secretion composition comprises in the range of approximately 0.01 µM to approximately 0.3 µM.

In a preferred embodiment, at least one of the first receptor activating compounds is adapted to induce at least 50% activation of at least OR51E1 in vivo when the GLP-1/GIP secretion composition is delivered to a patient.

In a preferred embodiment, at least one of the second receptor activating compounds is adapted to induce at least 50% activation of FFAR1 or FFAR4 in vivo when the GLP-1/GIP secretion composition is delivered to a patient.

In a preferred embodiment, when the GLP-1/GIP secretion compositions of the invention are delivered to a patient, the patient's appetite is similarly suppressed.

In some embodiments of the invention, there are also provided methods for treating type-2 diabetes mellitus and obesity comprising the steps of:

(a) providing one of the GLP-1/GIP secretion compositions of the invention; and (b) delivering the GLP-1/GIP secretion composition to a patient presenting with type-2 diabetes mellitus and obesity, whereby insulin secretion is induced, and appetite is suppressed.

In some embodiments of the invention, there are thus also provided methods of treating an endocrine disorder of a patient comprising the steps of (i) providing a GLP-1/PYY secretion composition of the invention, a GIP secretion composition of the invention, or a GLP-1/GIP secretion composition of the invention described above and (ii) delivering the composition(s) to the subject.

In some embodiments of the invention, there are also provided methods of treating obesity of a patient comprising the steps of (i) providing a GLP-1/PYY secretion composition of the invention, a GIP secretion composition of the invention, or a GLP-1/GIP secretion composition of the invention described above and (ii) delivering the composition(s) to the patient.

As indicated above, the GLP-1/PYY, GIP and GLP-1/GIP secretion compositions can be delivered to a patient via any suitable means, including, without limitation, oral, sublingual, inhalation, intranasal, epidural, intracerebral, transdermal, topical, and injection means.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A composition for treating an endocrine disorder of a patient, comprising:

a GLP-1/GIP secretion composition comprising (i) a delivery medium, (ii) at least a first receptor activating compound adapted to bind to and activate at least one first receptor selected from the group comprising olfactory receptor family 51 subfamily E member 1 (OR51E1) and olfactory receptor family 2 subfamily C member 1 (OR2C1), and (iii) at least a second receptor activating compound adapted to bind to and activate at least one second receptor selected from the group comprising free fatty acid receptor 1 (FFAR1) and free fatty acid receptor 4 (FFAR4), said GLP-1/GIP secretion composition adapted to induce glucagon-like peptide-1 (GLP-1) and gastric inhibitory polypeptide (GIP) secretion, and, thereby, increased insulin secretion in vivo, when said GLP-1/GIP secretion composition is delivered to said patient.

2. The composition of claim 1, wherein said at least a first receptor activating compound comprises eugenol.

3. The composition of claim 2, wherein said eugenol comprises a first $EC_{50}$ value of at least 0.1 µM in said GLP-1/GIP secretion composition.

4. The composition of claim 3, wherein said first $EC_{50}$ value of said eugenol comprises in the range of from about 0.1 µM to about 350.0 µM.

5. The composition of claim 3, wherein said eugenol is adapted to induce at least 50% activation of at least said olfactory receptor OR51E1 in vivo.

6. The composition of claim 1, wherein said at least a second receptor activating compound comprises a compound selected from the group consisting of a medium-chain free fatty acid, a long-chain free fatty acid and an omega-3 polyunsaturated fatty acid.

7. The composition of claim 6, wherein said medium-chain free fatty acid comprises lauric acid.

8. The composition of claim 7, wherein said lauric acid comprises a second $EC_{50}$ value of at least 0.05 µM in said GLP-1/GIP secretion composition.

9. The composition of claim 8, wherein said second $EC_{50}$ value of said lauric acid comprises in the range of from about 0.05 µM to about 50.0 µM.

10. The composition of claim 8, wherein said lauric acid is adapted to induce at least 50% activation of at least said free fatty acid receptor FFAR1 in vivo.

11. The composition of claim 1, wherein said composition comprises at least a third receptor activating compound adapted to bind to and activate said olfactory receptor OR51E1.

12. The composition of claim 11, wherein said at least a third receptor activating compound comprises butyl butyryl lactate.

13. The composition of claim 12, wherein said butyl butyryl lactate comprises a third $EC_{50}$ value of at least 0.1 µM in said GLP-1/GIP secretion composition.

14. The composition of claim 13, wherein said third $EC_{50}$ value of said butyl butyryl lactate comprises in the range of from about 0.1 µM to about 250.0 µM.

15. The composition of claim 1, wherein said GLP-1/GIP secretion composition further comprises at least a fourth receptor activating compound adapted to bind to and activate at least one third receptor selected from the group comprising olfactory receptor family 2 subfamily B member 11 (OR2B11), olfactory receptor family 2 subfamily J member 3 (OR2J3), and transient receptor potential cation channel subfamily A member 1 (TRPA1).

16. The composition of claim 15, wherein said at least a fourth receptor activating compound comprises cinnamaldehyde.

17. The composition of claim 16, wherein said cinnamaldehyde comprises a fourth $EC_{50}$ value of at least 0.1 µM in said GLP-1/GIP secretion composition.

18. The composition of claim 17, wherein said fourth $EC_{50}$ value of said cinnamaldehyde comprises in the range of from about 0.1 µM to about 2500.0 µM.

19. The composition of claim 17, wherein said cinnamaldehyde is adapted to induce at least 50% activation of said at least one third receptor in vivo.

20. The composition of claim 1, wherein said GLP-1/GIP secretion composition comprises at least a fifth receptor activating compound adapted to bind to and activate olfactory receptor family 2 subfamily W member 1 (OR2W1).

21. The composition of claim 20, wherein said at least a fifth receptor activating compound comprises benzyl acetate.

22. The composition of claim 21, wherein said benzyl acetate comprises a fifth $EC_{50}$ value of at least 0.1 µM in said GLP-1/GIP secretion composition.

23. The composition of claim 22, wherein said fifth $EC_{50}$ value of said benzyl acetate comprises in the range of from about 0.1 µM to about 100.0 µM.

24. The composition of claim 23, wherein said benzyl acetate is adapted to induce at least 50% activation of said olfactory receptor OR2W1 in vivo.

25. The composition of claim 1, wherein said delivery medium comprises glycerin-based water.

26. The composition of claim 1, wherein said delivery medium comprises ingestible matter selected from the group consisting of an item of food and a beverage.

* * * * *